United States Patent [19]

Patterson

[11] Patent Number: 5,827,659
[45] Date of Patent: Oct. 27, 1998

[54] METHODS AND APPARATUS FOR SEQUENCING POLYMERS USING MASS SPECTROMETRY

[75] Inventor: Dale H. Patterson, Nashua, N.H.

[73] Assignee: PerSeptive Biosystems, Inc., Framingham, Mass.

[21] Appl. No.: 796,598

[22] Filed: Feb. 7, 1997

Related U.S. Application Data

[63] Continuation of Ser. No. 446,055, May 19, 1995, abandoned.

[51] Int. Cl.$^6$ .............................. C12Q 1/68; C12Q 1/70; C12P 19/34; C07K 5/00
[52] U.S. Cl. .............................. 435/6; 435/5; 435/287.2; 435/288.7; 435/4; 435/91.1; 435/173; 422/99; 530/333; 530/300
[58] Field of Search .............................. 435/287.2, 288.7, 435/91.1, 6, 5, 4, 173; 530/333, 300; 422/99

[56] References Cited

U.S. PATENT DOCUMENTS

| | | | |
|---|---|---|---|
| 4,774,055 | 9/1988 | Wakatake et al. | 422/69 |
| 4,845,035 | 7/1989 | Fanta et al. | 435/178 |
| 4,882,127 | 11/1989 | Rosenthal et al. | 422/104 |
| 5,252,485 | 10/1993 | Zlobinsky et al. | 422/99 |
| 5,288,644 | 2/1994 | Beavis et al. . | |
| 5,474,796 | 12/1995 | Brennan | 422/104 |
| 5,622,824 | 4/1997 | Köster | 435/6 |

FOREIGN PATENT DOCUMENTS

WO93/24834  12/1993  WIPO .

OTHER PUBLICATIONS

Patterson et al. (1995), "Peptide Sequencing of Carboxypeptidase Digestion Coupled With MALDI–TOF," Abstract of presentation at the 43rd ASMS Conference, Atlanta, Georgia, May 25, 1995. (Applicants have informed Attorney that a computer disk containing the Abstract was mailed on May 9, 1995 by ASMS.).

Klarskov et al. (1989), "C–Terminal Sequence Determination of Peptides Degraded with Carboxypeptidases of Different Specificities and Analyzed by 252–Cf Plasma Desorption Mass Spectrometry," 180 *Analytical Biochemistry* 28–37.

Karas et al. (1990), "Principles and Applications of Matrix–Assisted UV–Laser Desorption/Ionization Mass Spectrometry," 241 *Analytica Chimica Acta* 175–185.

Woods et al. (1991), "Enzymatic Digestion on the Sample Foil as a Method for Sequence Determination by Plasma Desorption Mass Spectrometry: The Primary Structure of Porpoise Relaxin," 111 *International Journal of Mass Spectrometry and Ion Processes* 77–88.

Welch et al. (1991), "A Herpesvirus Maturational Proteinase, Assemblin: Identification of Its Gene, Putative Active Site Domain, and Cleavage Site," 88 *Proc. Natl. Acad. Sci. USA* 10792–10796.

Wang et al. (1992), "Determination of the Cleavage Site of the Amyloid Precursor Protein by Plasma Desorption Mass Spectrometry," *Techniques in Protein Chemistry III* (1992) (ed., R.H. Angeletti; Academic Press, N.Y.); pp. 505–513.

R.J. Cotter (1992), "Time of Flight Mass Spectrometry for the Structural Analysis of Biological Molecules," 64 *Analytical Chemistry* 1027A–1039A.

Woods et al. (1994), "Protein Processing in Herpes Virus," *Time of Flight Mass Spectrometry* (1994) (ed., R.J. Cotter; American Chemical Society, Washington, D.C.); pp. 194–210.

Aldrich et al. (1994), "Identification of a Tap–Dependent Leader Peptide Recognized by Alloreactive T Cells Specific for a Class 1b Antigen," 79 *Cell* 649–658.

Thiede et al. (1995), "MALDI–MS for C–Terminal Sequence Determination of Peptides and Proteins Degraded by Carboxypeptidase Y and P," 357 *Federation of European Biochemical Societies* 65–69.

Woods et al. (1995), "Simplified High–Sensitivity Sequencing of a Major Histocompatibility Complex Class I–Associated Immunoreactive Peptide Using Matrix–Assisted Laser Desorption/Ionization Mass Spectrometry," 226 *Analytical Biochemistry* 15–25.

PerSeptive Biosystems, Inc., Vestec Biospectrometry Products, 1994, "Voyager™Biospectrometry™ Workstation: High Throughput Accurate Mass Analysis Just Became Routine", Product Brochure.

Karas et al. Analytic Chimica Acta 241: 175–185, 1990.

PerSpective Biosystems Brochure, 1994.

*Primary Examiner*—W. Gary Jones
*Assistant Examiner*—Dianne Rees
*Attorney, Agent, or Firm*—Testa, Hurwitz & Thibeault, LLP.

[57] ABSTRACT

The methods and apparatus disclosed herein are useful for sequencing polymers using mass spectrometry. The methods involve differing ratios of hydrolyzing agent to polymer disposed upon a reaction surface adapted for use with a mass spectrometer. The methods further involve integrating data obtained from mass spectrometry analysis of a plurality of series of hydrolyzed polymer fragments, and optionally provide statistical interpretation paradigms and computer software therefor. The apparatus involves a mass spectrometer sample holder, having hydrolyzing agent disposed thereon, which is useful for adapting any mass spectrometer for polymer sequencing.

10 Claims, 16 Drawing Sheets

METHODS AND APPARATUS FOR SEQUENCING POLYMERS USING MASS SPECTROMETRY

This is a continuation of application Ser. No. 08/446,055 filed on May 19, 1995, now abandoned.

FIELD OF THE INVENTION

The present invention relates generally to methods and apparatus for sequencing polymers, especially biopolymers, using mass spectrometry.

BACKGROUND OF THE INVENTION

Biochemists frequently depend on reliable and fast determinations of the sequences of biological polymers. For example, sequence information is crucial in the research and development of peptide screens, genetic probes, gene mapping, and drug modeling, as well as for quality control of biological polymers when manufactured for diagnostic and/or therapeutic applications.

Various methods are known for sequencing polymers composed of two essential biological building-blocks, amino acids, carbohydrates and nucleotides. For example, existing methods for peptide sequence determination include the N-terminal chemistry of the Edman degradation, N- and C-terminal enzymatic methods, and C-terminal chemical methods. Existing methods for sequencing oligonucleotides include the Maxam-Gilbert base-specific chemical cleavage method and the enzymatic ladder synthesis with dideoxy base-specific termination method. Each method possesses inherent limitations that preclude it being used exclusively for complete primary structure identification. To date, Edman sequencing and adaptations thereof are the most widely used tools for sequencing certain protein and peptides residue by residue, while the enzymatic synthesis method is preferred for sequencing oligonucleotides.

In the case of protein and peptide sequencing, C-terminal sequencing via chemical methods has proven particularly difficult while being only marginally effective, at best. (See, e.g., Spiess, J. (1986) *Methods of Protein Characterization: A Practical Handbook* (Shively, J. E. ed., Humana Press, N.J.) pp. 363–377; Tsugita et al. (1994) *J. Protein Chemistry* 13:476–479). Consequently, the C-terminus remains a region often not analyzed because of lack of a dependable method.

In the case of both peptides and oligonucleotides, an alternate approach to chemical sequencing is enzymatic cleavage sequencing. In the case of oligonucleotides, over 150 different enzymes have been isolated and found suitable for preparing oligonucleotide fragments. In the case of peptides, serine carboxypeptidases have proven popular over the last two decades because they offer a simple approach by which amino acids can be sequentially cleaved residue by residue from the C-terminus of a protein or a peptide. Carboxypeptidase Y (CPY), in particular, is an attractive enzyme because it non-specifically cleaves all residues from the C-terminus, including proline. (See, e.g., Breddam et al. (1987) *Carlsburg Res. Commun.* 52:55–63.)

Sequencing of peptides by carboxypeptidase digestion has traditionally been performed by a laborious, direct analysis of the released amino acids, residue by residue. Not only is this approach labor-intensive, but it is complicated by amino acid contaminants in the enzyme and protein/peptide solutions, as well as by enzyme autolysis. A further hindrance to any sequencing effort of this type is the absolute requirement for good kinetic information concerning the hydrolysis and liberation of each individual residue by the particular enzyme used.

With the advancement of mass spectrometric techniques capable of high mass analysis such as field desorption (Hong et al. (1983) *Biomed. Mass Spectrom.* 10:450–457), electrospray (Smith et al. (1993) 4 *Techniques Protein Chem.* 463–470), and thermospray (Stachowiak et al. (1988) *J. Am. Chem. Soc.* 110:1758–1765), it is possible to perform direct mass analysis on large biopolymers such as the peptide fragments resulting from CPY digestion in which the sequence order is preserved, circumventing the need for residue by residue amino acid analysis of the liberated amino acids. In this "ladder" sequencing approach, a sequence can be deduced, in the correct order, by simply calculating the mass differences between adjacent peptide peaks, the measured differences representing the loss of a particular amino acid residue.

More recently, matrix-assisted laser desorption ionization time-of-flight (MALDI-TOF) mass spectrometry also was shown to be suitable for ladder sequence analysis due to its high sensitivity, resolution, and mass accuracy. Chait et al. ((1993) 262 *Science* 89–92) exploited these assets of MALDI-TOF in the ladder sequencing of N-terminal ladders formed from partial blockage at each step of chemical digestion by the Edman degradation method. This approach, however, still suffers from the same limitations of traditional Edman chemistry including the complexity of the process, the time-consuming nature of the process, and the lack of C-terminal information, however, it confirms the utility of MALDI-TOF for sequencing peptides using the peptide ladder scenario. Other researchers have also illustrated that carboxypeptidase digestion of peptides can be combined with MALDI-TOF to analyze the resulting mixture of truncated peptide. For example, eight consecutive amino acids have been sequenced from the C-terminus of human parathyroid hormone 1–34 fragment (Schar et al. (1991) *Chimia* 45:123–126). Additionally, carboxypeptidase digestion of peptides has been combined with other mass spectrometry methods such as plasma desorption (Wang et al. (1992) *Techniques Protein Chemistry III* (ed., R. H. Angeletti; Academic Press, N.Y.) pp. 503–515).

All of the above-described sequencing approaches, however, require preliminary optimization steps which are both tedious and time-consuming. Additionally, such preliminary optimization steps unnecessarily consume reagents as well as samples of polymer, usually available in limited quantities. Furthermore, the above-described sequencing approaches ultimately rely on a single mass spectrum and single mass-to-charge ratio data point, which can result in a statistically insufficient basis for determining a final polymer sequence.

It is an object of the present invention to provide methods and apparatus for sequencing polymers, particularly biopolymers, using mass spectrometry and time-independent/concentration-dependent hydrolysis of the polymer. It is an object of the present invention to also provide a rapid method for obtaining sequence information by circumventing the time-consuming optimization and method enhancement required by prior art methods. It is a further object of the present invention to provide sequence information using reduced quantities of total polymer by combining the sensitivity of mass spectrometry with elimination of sample loss by closely integrating hydrolysis with mass spectrometry analysis. It is another object of the present invention to provide a method for obtaining sequence information that incorporates a data interpretation strategy based on integrating mass-to-charge ratio data obtained from a plurality of parallel mass spectra.

SUMMARY OF THE INVENTION

The invention involves a novel form of sample holder for a mass spectrometer. The sample holder comprises a reaction surface with spacially separate areas having differing ratios of polymer and hydrolyzing agent. After a suitable incubation period during which the hydrolyzing agent hydrolyzes inter-monomer bonds within the polymer in each area, a plurality, typically all, of the areas containing hydrolyzed polymer fragments are ionized, typically serially, in the mass spectrometer and data representative of the mass to charge ratios of these fragments are obtained. One or more of the areas will have ratios of hydrolyzing agent to polymer suitable for more or less optimal generation of useful ladder elements or other polymer fragments. Some areas on the sample holder may have overly hydrolyzed polymer fragments useless for deriving sequence information. Other areas may contain substantially unhydrolyzed polymer. By mass spectrometry analysis of all areas, however, at least some mass to charge ratio data obtained from fragments generated in one or more areas which will contain useful data from which sequence information can be derived. Thus, by integrating the data from different areas, the method of the invention obviates the necessity to empirically prepare samples to ascertain the appropriate ratio of hydrolyzing agent to polymer, as well as optimal reaction time and carefully controlled reaction temperature, heretofore required. Furthermore, different hydrolyzing agents can be used in different series of areas on the sample holder so as to further generate useful hydrolyzed fragments, and the data from these may also be integrated to improve the sequencing process. If data analysis is implemented by a computer program, the whole process can be completed minutes after completion of the above-described incubation.

In one aspect, the present invention provides a method of obtaining sequence information about a polymer comprising a series of different monomers which involves: on a reaction surface, providing at least one amount of a hydrolyzing agent which hydrolyzes said polymer and breaks inter-monomer bonds, and a sample of polymer to form differing ratios of agent to polymer; incubating the same for a time sufficient to obtain a plurality of series of hydrolyzed polymer fragments; performing mass spectrometry on a plurality of the series to obtain mass-to-charge ratio data for hydrolyzed polymer fragments contained in the series; and integrating data from a plurality of the series to obtain sequence information characteristic of the polymer sample.

With regard to the aforementioned polymer, the instant invention contemplates both naturally-occurring and synthetic moieties characterized by a series of different monomers. In certain embodiments, the polymer is modified as described herein.

The method of the instant invention contemplates certain embodiments having hydrolyzing agents capable of hydrolyzing a polymer to form sequence-defining ladders, as well as certain other embodiments having hydrolyzing agents capable of forming polymer maps. In yet other embodiments, the instant invention provides for hydrolyzing the polymer with combinations of such agents. The instant method contemplates embodiments involving enzymatic as well as non-enzymatic hydrolyzing agents.

In one embodiment, the method provides that the hydrolyzing agent is disposed on the reaction surface in an array of discrete separate zones. In another embodiment, the hydrolyzing agent is disposed as a gradient. In yet another embodiment, the agent is disposed on the reaction surface in a constant amount. In other embodiments, polymer is similarly disposed on the reaction surface. In all embodiments, differing agent to polymer ratios are disposed upon the reaction surface and incubated to obtain a plurality of series of hydrolyzed polymer fragments. The various manners in which such differing ratios can be accomplished will be obvious to the skilled practioner.

In certain embodiments, the method provides combining the agent and polymer with other useful moieties. In one embodiment, moieties which selectively shift the mass of hydrolyzed fragments prior to mass spectrometry analysis are included. In another embodiment, moieties capable of improving ionization of hydrolyzed fragments are included. In yet another embodiment, the method provides for including a light-absorbent matrix. The instant method also contemplates embodiments in which any one or more of the above-described moieties are combined with the agent and polymer prior to mass spectrometry analysis.

It is further contemplated that the reaction surface is fabricated from a variety of substrates and assumes a variety of configurations suitable for use with a mass spectrometer. When practiced as disclosed herein, the method of the instant invention can be adapted to all manner of ion formation and all modes of mass analysis.

In another aspect, the present invention provides a mass spectrometer sample holder having a planar solid surface with at least one amount of a hydrolyzing agent capable of hydrolyzing a polymer disposed thereon. In one embodiment, the hydrolyzing agent is disposed on the reaction surface in a dehydrated form. In another embodiment, the hydrolyzing agent is immobilized on the reaction surface. In yet another embodiment, the hydrolyzing agent is disposed on the reaction surface in the form of a liquid or gel which is resistant to physical dislocation. In other embodiments, a light-absorbent matrix is disposed on the surface of the sample holder. Additionally, any one or more of such embodiments of the sample holder may further have microreaction vessels on their surface. Other embodiments of the sample holder of the instant invention are disposable.

As disclosed herein, all embodiments of the sample holder of the present invention are useful to adapt a mass spectrometry apparatus for obtaining sequence information about a polymer comprising a series of different monomers.

The method of obtaining sequence information in accordance with the instant invention solves problems encountered with conventional polymer sequence methodologies. For example, when conducting exopeptidase digestions in accordance with the instant method, the overall polymer sequencing effort is superior to the prior art time-dependent digestions in terms of: inherent simplicity of the method and elimination of laborious optimization requirements; reduced loss of sample due to transfer from reaction vessel to reaction surface; reduced amounts of enzyme and peptide used; and, particularly important for large-scale application, ease of use/automation.

Similarly, the mass spectrometry sample holder of the instant invention provides advantages heretofore unavailable to the skilled practitioner. For example, the sample holder minimizes reagent handling and greatly facilitates sample processing. The skilled practitioner need only provide a sample of polymer. Virtually all other experimental parameters are pre-optimized.

The foregoing and other objects, features and advantages of the present invention will be made more apparent from the following detailed description of preferred embodiments of the invention.

BRIEF DESCRIPTION OF THE DRAWINGS

The foregoing and other objects, features and advantages of the present invention, as well as the invention itself, will be more fully understood from the following description of preferred embodiments, when read together with the accompanying drawings, in which.

Detailed Description of Preferred Embodiments

Figure 1:
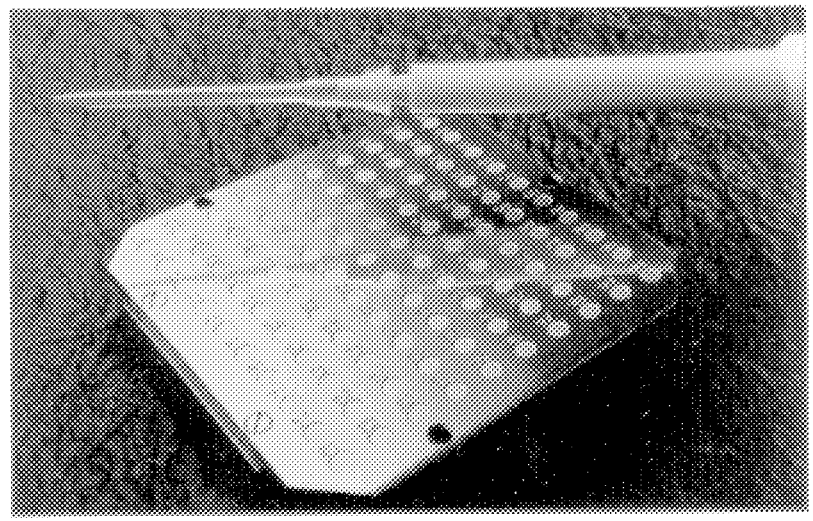
FIG. 1 is an exemplary sample plate for MALDI analysis.

As will be described below in greater detail, the instant invention relates to methods and apparatus for sequencing polymers using mass spectrometry. Specifically, the methods and apparatus utilize polymers and hydrolyzing agents disposed upon a reaction surface. The hydrolyzing agents are enzymatic or non-enzymatic. The hydrolyzing agents react with the polymer to produce sequence-defining polymer ladders or polymer maps. The methods of this invention further involve the step of obtaining mass spectrometry data relating to hydrolyzed polymer series and integrating the data from a plurality of polymer series to determine the polymer sequence. The mass spectrometry method of this invention is applicable to all manner of ion formation and all modes of mass analysis. The apparatus of this invention relates to a mass spectrometer sample holder for adapting a mass spectrometer to obtain sequence information about a polymer in accordance with the method of the instant invention. Specifically, the apparatus has disposed thereon hydrolyzing agent, in dehydrated, immobilized, liquid and/or gel form, and/or a light-absorbent matrix. Optionally, the apparatus of the instant invention is disposable.

As used herein, a "polymer" is intended to mean any moiety comprising a series of different monomers suitable for use in the method of the instant invention. That is, any moiety comprising a series of different monomers whose intermonomer bonds are susceptible to hydrolysis are suitable for use in the method disclosed herein. For example, a peptide is a polymer made up of particular monomers, i.e., amino acids, which can be hydrolyzed by either enzymatic or chemical agents. Similarly, a DNA is a polymer made up of other monomers, i.e., bases, which can be hydrolyzed by a variety of agents.

A polymer can be a naturally-occurring moiety as well as a synthetically-produced moiety. In a currently preferred embodiment, the polymer is a biopolymer selected from, but not limited to, the following group: proteins, peptides, DNAs, RNAs, PNAs (peptide nucleic acids), carbohydrates, and modified versions thereof.

"Sequence information" as used herein is intended to mean any information relating to the primary arrangement of the series of different monomers within the polymer, or within portions thereof. Sequence information includes information relating to the chemical identity of the different monomers, as well as their particular position within the polymer. Polymers with known primary sequences, as well as polymers with unknown primary sequences, are suitable for use in the methods of the instant invention. It is contemplated that sequence information relating to terminal monomers as well as internal monomers can be obtained using the methods disclosed herein. In certain applications, sequence information can be obtained using a sample of an intact, complete polymer. In other applications, sequence information can be obtained using a sample containing less than the intact complete polymer, for example, polymer fragments. Such fragments can be naturally-occurring, artifacts of isolation and purification, and/or generated in vitro by the skilled artisan. Additionally, polymer fragments can be initially derived from and prepared by a variety of fractionation and separation methods, such as high performance liquid chromatography, prior to use with the methods of the instant invention.

The "reaction surface" of the instant method includes any surface suitable for hydrolyzing the subject polymer with the subject agent. The reaction surface can be fabricated from a variety of substrates, such as but not limited to: metals, foils, plastics, ceramics, and waxes. All reaction surfaces must be suitable for use with a mass spectrometer apparatus. The reaction surface of the instant invention can assume any configuration suitable for use with a particular mass spectrometer apparatus. For example, the reaction surface can be a planar solid surface. Alternatively, the surface may have microreaction vessels disposed thereon. In yet another embodiment, the reaction surface can assume the configuration of a probe suitable for use with certain mass spectrometer apparatus. In some embodiments, the skilled artisan will appreciate that the reaction surface can be activated and/or derivatized to enhance or facilitate polymer sequencing in accordance with the instant invention.

As used herein, the term "hydrolyzing agent" is intended to mean any agent capable of disrupting inter-monomer bonds within a particular polymer. That is, any agent which can interrupt the primary sequence of a polymer is suitable for use in the methods disclosed herein. Hydrolyzing agents can act by liberating monomers at either termini of the polymer, or by breaking internal bonds thereby generating fragments or portions of the subject polymer. Generally, a preferred hydrolyzing agent interrupts the primary sequence by cleaving before or after a specific monomer(s); that is, the agent specifically interacts with the polymer at a particular monomer or particular sequence of monomers recognized by the agent as the preferred hydrolysis site within the polymer. All of the currently preferred hydrolyzing agents described herein are commercially available from reagent suppliers such as Sigma Chemicals (St. Louis, Mo).

In some preferred embodiments, an excipient is added to, and used in conjunction with, the hydrolyzing agent. The excipients contemplated herein facilitate lyophilization and/or dissolution of the hydrolyzing agent. For example, fucose and other sugars suitable for use with the instant invention are contemplated. Suitable for use is intended to mean that no interference with mass spectrometry is encountered by the use thereof. Other excipients useful in the instant invention are pH modifiers, such as ammonium acetate. Still other excipients suitable for use in the methods and apparatus disclosed herein are those which act as stabilizers of the integrity of the hydrolyzing agent. With respect to excipients, the identity of those suitable will be obvious to the skilled artisan using only routine experimentation. While certain preferred excipients are described above, identification of suitable equivalents is within the skill of the ordinary artisan.

In one currently preferred embodiment, the hydrolyzing agent is a hydrolase enzyme. Some hydrolases are endohydrolases, others are exohydrolases. The particular hydrolase used is determined by the nature of the polymer and/or the type of sequence information desired. Its identity can be readily determined by the skilled artisan using no more than routine experimentation. For example, currently preferred endohydrolases include but are not limited to: endonucleases, endopeptidases, endoglycosidases, trypsin, chymotrypisin, endoproteinase Lys-C, endoproteinase Arg-C, and thermolysin. Currently preferred exohydrolases include but are not limited to: exonucleaes, exoglycosidases, and exopeptidases. The currently preferred exonucleases include, but are not limited to: phosphodiesterase types I and II, exonuclease VII, λ-exonuclease, T7 gene 1 exonuclease, exonuclease III, BAL-31, exonuclease I, exonuclease V, exonuclease II, and DNA polymerase III. The currently preferred exoglycosidases include, but are not limited to: α-mannosidase I, α-mannosidase, β-hexosaminidase, β-galactosidase, α-fucosidase I, α-fucosidase II, α-galactosidase, α-neuraminidase, α-glucosidase I and α-glucosidase II. The currently preferred exopeptidases include, but are not limited to: carboxypeptidase Y, carboxypeptidase A, carboxypepetidase B, carboxypeptidase P, aminopeptidase 1, leucine amino peptidase, proline aminodipeptidase, and cathepsin C.

In certain other embodiments, the hydrolyzing agent is an agent other than an enzyme. For example, such an agent can be a chemical, such as an acid. Currently preferred agents other than an enzyme include but are not limited to: cyanogen bromide, hydrochloric acid, sulfuric acid, and pentafluoroproprionic fluorohydride. In some embodiments, hydrolysis can be accomplished using partial acid hydrolysis in accordance with the methods disclosed herein. Again, the identity of a hydrolyzing agent other than an enzyme will be determined by the nature of the polymer and the type of sequence information desired. It is within the skilled practitioner's ability to identify a suitable agent, as well as the circumstances under which such an agent is preferred.

The instant method further provides for use of combinations of the above-described individual hydrolyzing agents. For example, combinations of enzymes can be used in the claimed invention. Combinations of hydrolyzing agents other than enzymes can also be used. Furthermore, combinations of enzymes with agents other than enzymes can also be used in the instant method. Again, the exact combination and the circumstances under which such a combination is appropriate will depend upon the nature of the polymer and the sequence information desired. The skilled practitioner will know when combinations of hydrolyzing agents are suitable for use in the methods disclosed herein.

Numerous examples of hydrolyzing agent/polymer sequence-specific interactions are well known in the art. For example, as described above, currently preferred polymers such as proteins and DNAs specifically interact with proteinases and nucleases, respectively. Certain of the preferred proteinases specifically recognize the C-terminus (carboxypeptidase Y) or the N-terminus (amino peptidase 1) of a protein's amino acid sequence. Certain of the preferred nucleases specifically recognize the 5' or the 3' terminus of a polynucleotide's base sequence. Some nucleases recognize single-stranded polynucleotides; others recognize double-stranded polynucleotides while still others recognize both.

In accordance with the instant invention, such exohydrolases generate a series of hydrolyzed fragments comprising a sequence-defining "ladder" of the polymer. That is, these agents generate a series of hydrolyzed fragments, each hydrolyzed fragment within the series being a "ladder element," which collectively comprise a sequence-defining "ladder" of the polymer. Ladder elements represent hydrolyzed fragments from which monomers have been consecutively and/or progressively liberated by the exohydrolase acting at one or the other of the polymer's termini. Accordingly, ladder elements are truncated hydrolyzed polymer fragments, and ladders per se are concatenations of these collective truncated hydrolyzed polymer fragments. In this manner, for example, sequence information relating to the amino acid sequence of a protein can be obtained using carboxypeptidase Y, an agent which acts at the carboxy terminus. By using the methods disclosed herein to generate a series of protein hydrolysates related one to the other by consecutive, repetitive liberation of amino acid residues, the skilled artisan can reconstruct the primary sequence of the intact protein polymer as described in further detail below.

Similarly, hydrolyzing agents other than exohydrolases which also act at one or the other of a polymer's termini generate ladder elements which collectively comprise a series of sequence-defining ladders. For example, the well-known Edman degradation technique and associated reagents can be adapted for use with the methods of the instant invention for this purpose. Thus the above-described subtractive-type sequencing method, through which repetitive removal of successive amino-terminal residues from a protein polymer can occur, can also be accomplished with hydrolyzing agents other than enzymes as disclosed herein.

As previously described, sequence information can also be obtained using hydrolyzing agents which act to disrupt internal inter-monomer bonds. For example, an endohydrolase can generate a series of hydrolyzed fragments useful ultimately in constructing a "map" of the polymer. That is, this agent generates a series of related hydrolyzed fragments which collectively contribute information to a sequence-defining "map" of the polymer. For example, peptide maps can be generated by using trypsin endohydrolysis in tandem with cyanogen bromide endohydrolysis to obtain hydrolyzed fragments with overlapping amino acid sequences. Such overlapping fragments are useful for reconstructing ultimately the entire amino acid sequence of the intact polymer. For example, this combination of hydrolyzing agents generates a useful plurality of series of hydrolyzed fragments because trypsin specifically catalyzes hydrolysis of only those peptide bonds in which the carboxyl group is contributed by either a lysine or an arginine monomer, while cyanogen bromide cleaves only those peptide bonds in which the carbonyl group is contributed by methionine monomers. Thus, by using trypsin and cyangogen bromide hydrolysis in tandem, one can obtain two different series of hydrolyzed "mapping" fragments. These series of mapping fragments are then examined by mass spectrometry to identify specific hydrolysates from the second cyanogen bromide hydrolysis whose amino acid sequences establish continuity with and/or overlaps between the specific hydrolysates from the first hydrolysis with trypsin. Overlapping sequences from the second hydrolysis provide information about the correct order of the hydrolyzed fragments produced by the first trypsin hydrolysis. While these general principles of peptide mapping are well-known in the prior art, utilizing these principles to obtain sequence information by mass spectrometry as disclosed herein has heretofore been unknown in the art.

It will be obvious to the skilled artisan that certain sequencing determinations will be best accomplished using the above-described ladder scenario, while others will be better suited to the mapping scenario. In some situations, a combination of the ladder and mapping sequencing methodologies taught herein will provide optimum sequence information. Using only routine experimentation, the skilled artisan will be able to obtain optimum sequence information using the ladder and/or mapping methods in conjunction with mass spectrometry analysis of a plurality of the series of hydrolyzed polymer fragments.

As contemplated by the instant method, a sample of polymer includes biological fluids containing (or suspected to contain) the polymer of interest. As used herein, a sample of polymer is also intended to include isolated and purified polymer. Additionally, a sample of polymer can be aqueous or non-aqueous.

Adding a sample of polymer to the reaction surface can be accomplished in a variety of ways. For example, the sample can be introduced as individual aliquots, or the sample can be introduced in a continuous mode such as sample eluting from a preparative or qualitative column. In both cases, the sample can be introduced manually or by automated means.

Upon adding a sample of polymer and hydrolyzing agent to the reaction surface, the instant method provides that differing concentrations of agent or ratios of agent to polymer are formed on said reaction surface. For example, if the polymer sample contains a uniform amount of polymer, then the method contemplates that differing amounts of agent be disposed on the reaction surface. This would produce differing agent to polymer ratios. The differing amounts of agent can be in the form of discrete separate zones to which a constant amount of polymer is added. Alternatively, the differing amounts of agent can be in the form of a non-discrete gradient of agent ranging from low to high amounts of agent, perhaps in the form of strip of appropriate length and width. By introducing a strip of polymer of equal length and width which contains a constant amount of polymer, differing agent to polymer ratios are produced. As contemplated herein, the agent and polymer can assume any configuration and be present in any amount(s); all that is required is that the combination of agent and polymer results in differing ratios of the same disposed on the reaction surface. It will be obvious to the skilled artisan that differing ratios of agent to polymer can also be accomplished by disposing a constant amount of agent on the reaction surface and adding varying amounts of polymer, e.g., a polymer gradient or discrete separate zones of differing amounts of polymer or polymer solution. In the case of a polymer gradient, polymer eluted from a column in the form of a gaussian-distributed gradient is currently preferred.

The instant method further provides for incubating the above-described agent to polymer ratios for a time required to obtain the requisite plurality of series of hydrolyzed polymer fragments. Incubating can proceed under any conditions suitable for hydrolyzing the polymer and for any amount of time required to obtain a plurality of series of hydrolyzed fragments. Generally speaking, the disclosed methods permit sequencing information to be obtained in relatively short time periods, for example, in less than 1 hour. The incubation time, however, can be shortened or lengthened depending upon the nature of the polymer and/or hydrolyzing agent(s). It will be obvious to one skilled in the art how to identify appropriate incubation times and optimize the same. Incubation reactions can be terminated by evaporation.

As used herein, a "plurality of series" of hydrolyzed polymer fragments is intended to mean that hydrolyzed fragments are produced by at least two different agent:polymer ratios, and that each agent:polymer ratio generates a series of hydrolyzed fragments. For example, if a constant amount of polymer is added to two separate zones of agent containing different amounts of agent, each zone represents one agent:polymer ratio and each zone produces one series of hydrolyzed fragments. When taken together, the two zones are a plurality which collectively contain a plurality of series of hydrolyzed polymer fragments.

The method disclosed herein teaches obtaining sequence information by performing mass spectrometry on a plurality of series of hydrolyzed fragments to obtain mass-to-charge ratio data for hydrolyzed polymer fragments contained therein. As already discussed, this contemplates that at least two different agent:polymer ratios be provided and analyzed by mass spectrometry.

Any manner of ion formation can be adapted for obtaining mass-to-charge ratio data, including but not limited to : matrix-assisted laser desorption ionization, plasma desorption ionization, electrospray ionization, thermospray ionization, and fast atom bombardment ionization. Additionally, any mode of mass analysis is suitable for use with the instant invention including but not limited to: time-of-flight, quadrapole, ion trap, and sector analysis. A currently preferred mass spectrometer instrument is an improved time-of-flight instrument which allows independent control of potential on sample and extraction elements, as described in copending U.S. Ser. No. 08/446,544 (Atty. Docket No. SYP-111) filed on even date herewith and which is herein incorporated by reference.

As disclosed herein, mass-to-charge ratio data are obtained using a plurality of series of hydrolyzed fragments. Thus, as discussed earlier, hydrolyzed fragments from at least two different agent:polymer ratios are provided to obtain mass-to-charge ratios by mass spectrometry. Similarly, the mass-to-charge ratio data from at least two different agent: polymer ratios are integrated to obtain the sequence information characteristic of the polymer. As discussed in further detail below, integrating data in accordance with the instant invention to obtain sequence information is more accurate, efficient, and rapid than sequence methods heretofore known in the art.

The method of the instant invention also provides for including moieties useful in mass spectrometry. For example, a light-absorbent matrix can be introduced at any point prior to performing mass spectrometry analysis by laser desorption. Light-absorbent matrices are particularly useful for analysis of biopolymers. Matrix-assisted laser desorption ionization techniques, as well as various matrices suitable therefor, are well known in the art and have been described, for example, in U.S. Pat. No. 5,288,644 (issued Feb. 22, 1994) and U.S. Ser. No. 08/156,316 (Atty. Docket No. Vestec-14-2, allowed Apr. 18, 1995), the disclosures of which are herein incorporated by reference.

Other moieties useful in the instant method include those capable of selectively shifting the mass of certain hydrolyzed fragments. These, too, can be added at any point prior to mass spectrometry analysis. Currently preferred mass-shifting moieties include, but are not limited to, those moieties which produce reaction products such as: alkyl, aryl, alkenyl, acyl, thioacyl, oxycarbonyl, carbamyl, thiocarbamyl, sulfonyl, imino, guanyl, ureido, and silyl reaction products. Attachment of such moieties to hydrolyzed polymers is achieved using art-recognized attachment chemistries. The particular moiety best suited to a particular sequence determination will depend upon the nature of the polymer and the hydrolyzed fragments. The skilled artisan will be able to determine which moiety to use, if any.

Another group of moieties suitable for use with the instant method are those which can improve ionization of hydrolyzed fragments. Such moieties can be introduced at any time prior to mass spectrometry analysis. Currently-preferred ionization-improving moieties include, but are not limited to, those moieties which produce reaction products such as: amino, quarternary amino, pyridino, imidino, guanidino, oxonium, and sulfonium reaction products. Preparation and/or use of such moieties are well known in the art.

In another aspect, the instant invention provides a mass spectrometer sample holder. The instant sample holder is useful for adapting any mass spectrometer apparatus for obtaining sequence information in accordance with the disclosed methods. In one currently preferred embodiment, the sample holder has a planar solid surface on which is disposed hydrolyzing agent. In another currently preferred embodiment, the sample holder has the form of a probe useful in certain mass spectrometer apparatus. In all embodiments of the sample holder, the agent can be in dehydrated, immobilized, liquid and/or gel form. In embodiments having agent in liquid or gel form, the agent is resistant to physical dislocation and is chemically stable for at least about one to two months, thereby facilitating both transport and storage. These considerations are particularly useful for commercial applications involving the sample holder of the present invention. Furthermore, the agent can be disposed in separate discrete zones of differing amounts, or in a non-discrete gradient. Alternatively, the agent can be disposed in a constant amount on the surface of the sample holder. In other embodiments, the sample holder has a light-absorbent matrix disposed on its surface; this can be with or without hydrolyzing agent.

The sample holder can also have microreaction vessels arranged on its surface. In one embodiment, these vessels can be depressions on the holder's surface resulting from chemical-etching or similar techniques. The sample holder can be fabricated from a variety of substrates including but not limited to: metals, foils, plastics, ceramics, and waxes. In certain embodiments, the sample holder is disposable. In certain other embodiments, the sample holder disclosed herein is a component of a kit useful for sequencing polymers by mass spectrometry, such as that disclosed in co-pending U.S. Ser. No. 08/447,175 (Atty. Docket No.: SYP-114) filed on even date herewith and herein incorporated by reference.

The instant invention also relates to a method of data analysis of the mass-to-charge ratios obtained by mass spectrometry. As described in further detail below (and in co-pending U.S. Ser. No. 08/447,175, (Atty. Docket No. SYP-114) filed on even date herewith and herein incorporated by reference), the method provides a set of fragments, created by hydrolysis of the polymer, each set differing by one or monomers. The difference between the mass-to-charge ratio of at least one pair of fragments is determined. One then asserts a mean mass-to-charge ratio which corresponds to the known mass-to-charge ratio of one or more different monomers. The asserted mean is compared with the measured mean to determine if the two values are statistically different with a desired confidence level. If there is a statistical difference, then the asserted mean difference is not assignable to the actual measured difference. In some embodiments, additional measurements of the difference between a pair of fragments are taken, to increase the accuracy of the measured mean difference. The steps of the method are repeated until one has asserted all desired mean differences for a single difference between one pair of fragments. The method is repeated for additional pairs of fragments and the mass-to-charge ratio data from a plurality of parallel mass spectra are integrated until the desired sequence information is obtained.

Practice of the invention will be still more fully understood from the following examples, which are presented herein for illustration only and should not be construed as limiting the invention in any way.

EXAMPLE 1. MATERIALS AND METHODS (a) Solution-Phase Digestion of ACTH 7–38 Fragment For the time course digestion, 500 pmol of synthetic human adrenocorticotropic hormone (ACTH) fragment (7–38) [PheArgTrpGlyLysProValGlyLysLysArgArgProValLysVal] (SEQ. ID. No:22) from Sigma Chemical Company (St. Louis, Mo), previously dried down in a 0.5 mL eppendorf vial, was resuspended with 33.3 $\mu$L of HPLC grade water (J. T. Baker, Phillipsburg, N.J.). In a previously dried down 0.5 mL eppendorf tube, 3.05 units (one unit hydrolyzes 1.0 $\mu$mol N-CBZ-phe-ala to N-CBZ-phenylanine+alanine per minute at pH=6.75 and 25° C.) of carboxypeptidase Y from bakers yeast (E.C. 3.416.1), purchased from Sigma, was resuspended with 610 $\mu$L of HPLC grade water. To 20 $\mu$L of the ACTH 7–38 fragment solution was added 10 $\mu$L of the CPY solution to initiate the reaction. The final concentrations were 10 pmol/$\mu$L ACTH and $1.67 \times 10^{-3}$ units/$\mu$L CPY yielding an enzyme-to-substrate ratio of $1.67 \times 10^8$ units CPY/mol ACTH (1:37 molar ratio assuming CPY MW=61,000). Aliquots of 1 $\mu$L were taken from the reaction vial at reaction times of 15 s, 60 s, 75 s, 105 s, 2 min, 135 s, 4 min, 5 min, 6 min, 7 min, 8 min, 9 min, 10 min, 15 min and 25 min. At 25 min, 15 $\mu$L of $5 \times 10^{-3}$ units/$\mu$L CPY was added to the reaction vial. Aliquots of 2 $\mu$L were removed at total reaction times of 1 hr and 24 hr. The reaction proceeded at room temperature until 2 min when the temperature was elevated to 37° C. All aliquots were added to 9 $\mu$L of the MALDI matrix, α-cyano-4-hydroxy cinnamic acid (CHCA) from Sigma, at a concentration of 5 mg/mL in 1:1 acetonitrile (ACN):0.1% trifluoroacetic acid (TFA) with the exception of the 1 hr and 24 hr aliquots were added to 8 $\mu$L of the matrix. The final total peptide concentrations of the ACTH digestion aliquots in the matrix solutions were 1 pmol/$\mu$L. A pooled peptide solution was prepared by combining 2 $\mu$L of the 15 s, 105 s, 6 min and 25 min aliquots. Into individual $\mu$L wells on the MALDI sample plate, 1 $\mu$L of each aliquot solution was placed and allowed to evaporate to dryness before insertion into the mass spectrometer.

(b) On-Plate Digestions:

All on-plate digestions were performed by pipetting 0.5 $\mu$L of the peptide at a concentration of 1 pmol/$\mu$L into each of ten 1 $\mu$L wells across one row of a sample plate configured similarly to the sample plate manufactured and supplied by PerSeptive BioSystems, Inc. of Framingham, Mass. and adapted for use with their trademarked mass spectrometry apparatus known as Voyager™. All peptides listed in Table 1 were purchased from Sigma and were of the highest purity offered. To initiate the reaction in the first well, 0.5 µL of 0.0122 units/µL CPY was added. To the subsequent 9 wells was added CPY at concentrations of $6.10 \times 10^{-3}$, $3.05 \times 10^{-3}$, $1.53 \times 10^{-3}$, $6.10 \times 10^{-4}$, $3.05 \times 10^{-4}$, $1.53 \times 10^{-4}$, $7.63 \times 10^{-5}$, $3.81 \times 10^{-5}$ and 0 units/µL, respectively. Mixing was assured in each well by pulling the 1 µL reaction back and forth through the pipet tip. The reaction was allowed to proceed at room temperature until the 1 µL total volume evaporated on the plate (approximately 10 min). At such time, 1 µL of 5mg/mL CHCA in 1:1 ACN:0.1% TFA was added to each well, with no further mixing, and allowed to evaporate for approximately 10 min before mass analysis.

(c) MALDI-TOF Mass Spectrometry:

MALDI-TOF mass analysis was performed using the Voyager™ Biospectrometry™ Workstation (PerSeptive Biosystems, Cambridge, Mass.). A 28.125 KV potential gradient was applied across the source containing the sample plate and an ion optic accelerator plate in order to introduce the positively charged ions to the 1.2 m linear flight tube for mass analysis. For the data acquisition of the ACTH 7–38 fragment and glucagon digests, a low mass gate was used to prevent the matrix ions from striking the detector plate. For the application of the low mass gate, the guide wire was pulsed for a brief period deflecting the low mass ions (approximately <1000 daltons). All other spectra were recorded with the low mass gate off. To enhance the signal-to-noise ratio, 64–128 single shots from the nitrogen laser (337 nm) were averaged for each mass spectrum. The data presented herein were smoothed using an 11 point Savitsky-Golay second order filter. All data was calibrated using an external calibration standard mixture of bradykinin ($MH^+$= 1061.2) and insulin B-chain, oxidized ($MH^+$=3496.9) (both purchased from Sigma) at concentrations of 1 pmol/µL in the 5 mg/mL CHCA matrix solution.

(d) Statistical Mass Assignments:

As described in further detail below, the statistical protocol disclosed herein uses the equation for the two-tailed t-test:

$$t_{calculated} = \frac{|\bar{x} - \mu|/\sqrt{2}}{s}$$

where $\bar{x}$ is the average experimental mean, $\mu$ is the asserted mean, n is the number of replicates and S is the experimental standard deviation. For the assignment of residues to experimentally derived Δ masses, a $t_{calculated}$ for each asserted mean mass (each possible amino acid assignment) was compared to the tabulated value for a given confidence interval. A $t_{calculated} > t_{table}$ indicated that the experimental mass came from a population possessing a different mean than the asserted mass at the given confidence level.

Figure 2A:
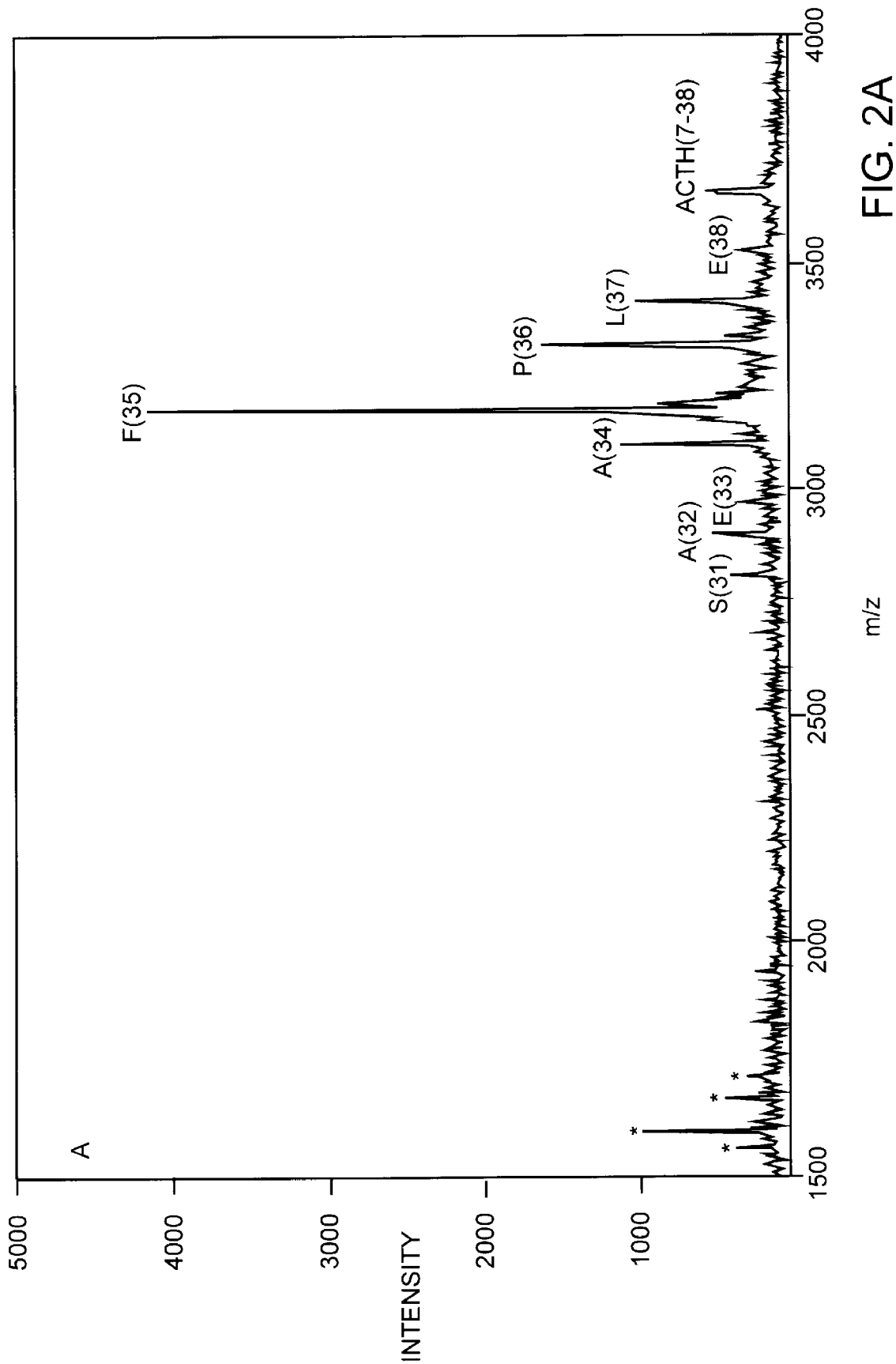
FIGS. 2A, 2B and 2C depict several MALDI spectra from a time-dependent CPY digestion of ACTH 7–38 fragment [PheArgTrpGlyLysProValGlyLysLysArgArsProValLysVal] SEQ ID NO: 22 at 1 min (2A), 5 min (2B) and 25 min (2C).
Figure 2B:
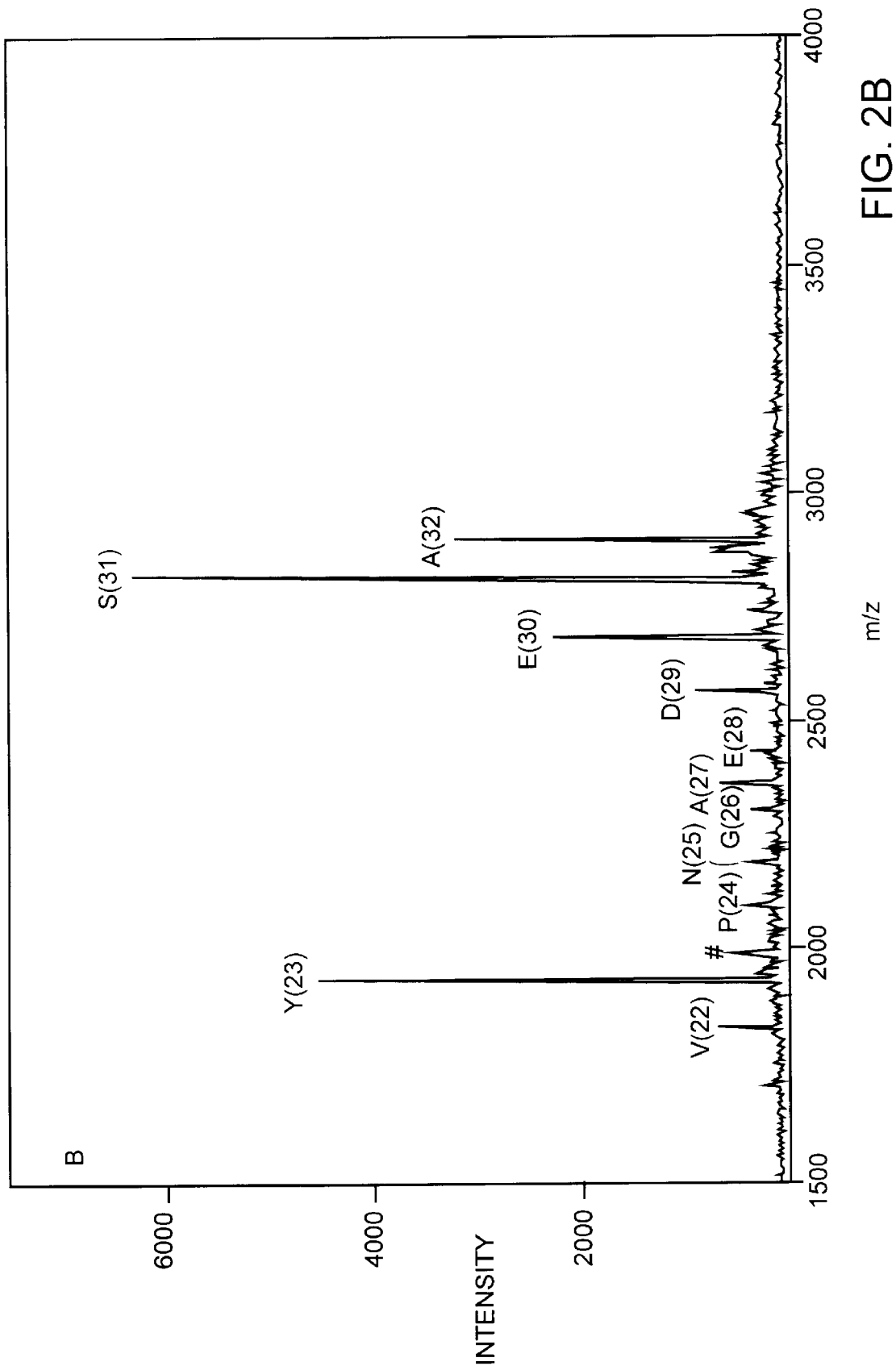

EXAMPLE 2. SEQUENCING OF BIOPOLYMERS (a) Solution-Phase Sequencing:

FIG. 2 illustrates the MALDI spectra of the 1 min, 5 min and 25 min time aliquots that were removed from a solution-phase time-dependent CPY digestion of ACTH 7–38 fragment. The nomenclature of the peak labels denotes the peptide populations resulting from the loss of the indicated amino acids. Peaks representing the loss of 19 amino acids from the C-terminus are observed. The symbol * indicates doubly charged ions and # indicates an unidentified peak at m/z=2001.0 and 2744.4 daltons.

Figure 2C:
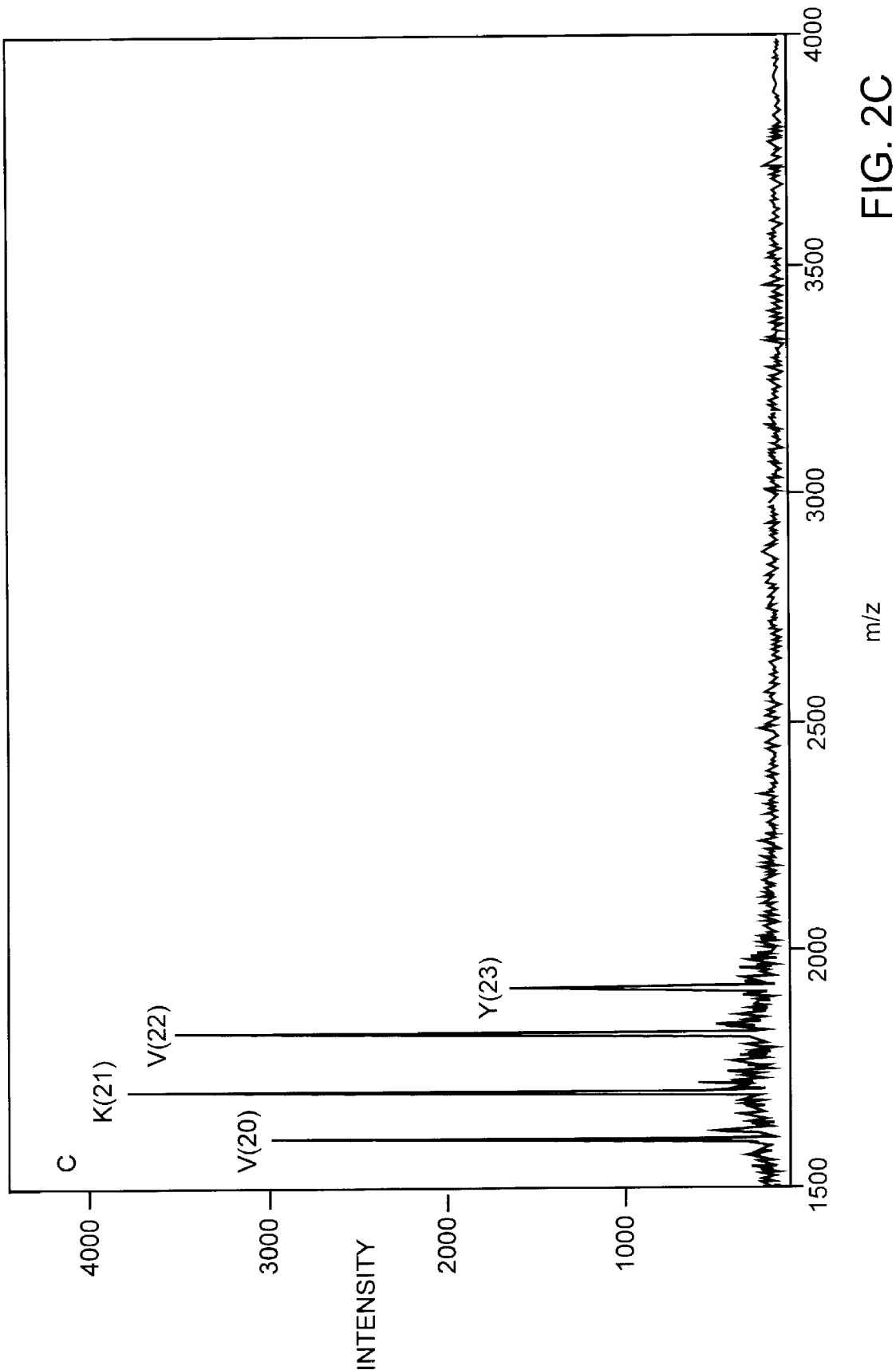

The lack of phase control of the enzymatic digestion creates the peptide ladders that are observed in this figure. After 1 min of digestion (FIG. 2A), 9 detectable peptide populations exist including the intact ACTH 7–38 fragment and peptides representing the loss of the first 8 amino acids from the C-terminus. The 5 min aliquot (FIG. 2B) shows that the peptide populations representing the loss of Ala(32) and Ser(31) have become much more predominant than the 1 min aliquot. Amino acid losses of 11 residues, Ala(32) through Val(22), are present at this digestion time. FIG. 2C shows the final detected amino acids of Lys(21) and Val(20) as 4 major peptide populations are detected. Upon increasing the enzyme concentration 2-fold at 25 min, no further digestion was observed through 24 h. The digestion proceeded through the Val(20) and stopped at the amino acid run of peptide-KKRRP. Although CPY may proceed rapidly through proline (e.g., Pro(24)), the basic residue, arginine, at the penultimate position in this case proved to be a combination refractory to CPY.

The lack of phase control coupled with the varied rates of hydrolysis poses problems unique to enzymatic sequencing. Varying ion intensities for the peaks in FIG. 2 are due primarily to the rates of hydrolysis that vary according to the amino acids at the C-terminus and penultimate position. When a residue is hydrolyzed at a low rate compared to the neighboring residues, the concentration and, therefore, signal of the peptide population representing the loss of that residue will be small relative to that of the preceding amino acid. This is seen in the mass spectra given in FIG. 2. The cleavage of Ala(34) is shown to be slow resulting in the large signal representing the loss of Phe(35). The hydrolysis of glycine and valine are also shown to be slow as the peaks representing the loss of Ala(27) and Tyr(23) are comparatively more intense than those of Gly(26) and Val(22), respectively.

The prior-art time-dependent method presented herein is the result of extensive method optimization and is optimized for obtaining the maximum sequence information in the shortest amount of time. For this particular optimized case, detectable amounts of all populations were observed over 25 min in the three selected time aliquots. This was not the case for numerous preliminary solution-phase digestions that were performed during the method optimization that led to the choice of these optimized conditions. At higher concentrations of CPY the peaks representing the loss of Glu(28) and Pro(24) were often not observed, indicating that CPY cleaves these residues very readily when alanine and tyrosine are at the penultimate positions, respectively. Lower concentrations of CPY allowed for all amino acids to be sequenced but often required long periods of time, e.g., days, for sufficient digestion. In the instance disclosed herein, an enzyme-to-substrate ratio of $1.67 \times 10^8$ units CPY/mole peptide was finally found to offer sufficient sequence information in 25 min of digestion.

Figure 3:
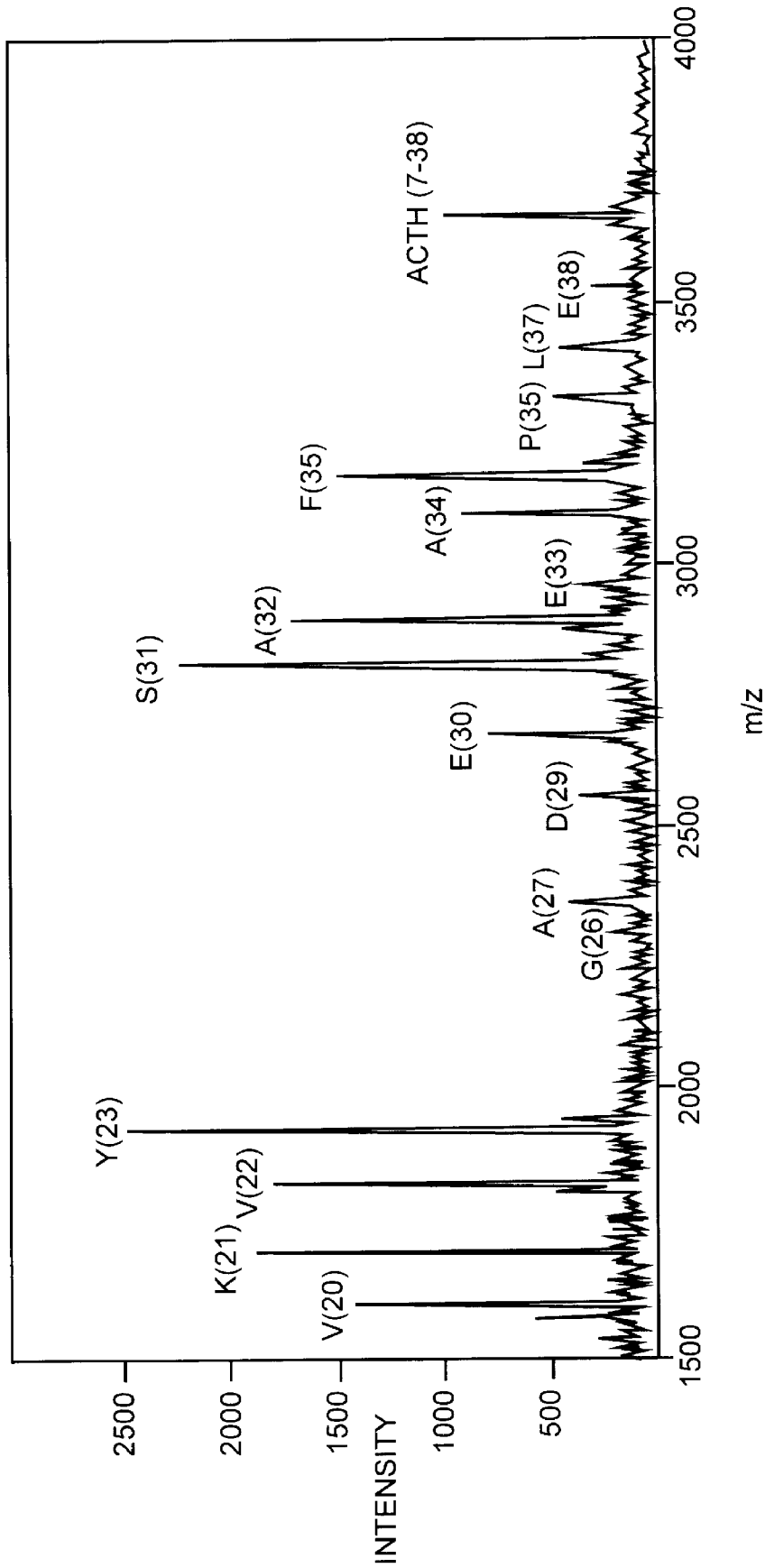
FIG. 3 is a MALDI mass spectrum representing pooled 15 s, 105 s, 6 min and 25 min quenched aliquots.

Alternatively, upon pooling aliquots from 15 s, 105 s, 6 min, and 25 min of total reaction time, MALDI analysis shows that a peptide ladder is formed that contains peaks that represent the loss of almost all amino acids from the C-terminus (FIG. 3). All amino acid losses are observed except for those of Glu(28), Asn(25), and Pro(24) which were present as small peaks in the 6 min aliquot and subsequently diluted to undetectable concentrations in this pooled fraction.

A sequence gap is observed here as the peptide populations representing the loss of Glu(28), Asn(25) and Pro(24) exist below a signal-to-noise ratio of 3. These populations were observed as small peaks in the 6 min aliquot mass spectrum but, upon the 4-fold dilution with the other aliquots, exist in too small a concentration to be detected. This emphasizes the necessity of recording individual mass spectra for each time aliquot. The less time-demanding procedure of recording a single spectrum representing pooled results not only created sequence gaps, but lost the time-dependent history of the digestion.

As illustrated above, solution-phase digestion suffers from a number of disadvantages. A large amount of time, enzyme and peptide is required for method optimization in order to obtain significant digestion in a short amount of time while preserving all possible sequence information. For each peptide from which sequence information is to be derived, some time-consuming method development must be performed since a set of optimum conditions for one peptide is not likely to be useful for another peptide given the composition-dependent hydrolysis rates of CPY. An alternative strategy is to perform the concentration-dependent hydrolysis on the MALDI sample surface as described below.

(b) On-Plate Sequencing:

FIG. 1 depicts a voyager™ sample plate for MALDI analysis comprised of a 10×10 matrix of 1 μL wells etched into the stainless steel base. These wells serve as micro-reaction vessels in which on-plate digestions may be performed. The physical dimensions of the plate are 57×57 mm and the wells are 2.54 mm in diameter.

Half-μL amounts of both enzyme and substrate were placed in a well and mixed with the pipet tip. The digestion continued for about 10 min until solvent evaporation terminates the reaction. At this time, the digestion mixture was resuspended by placing 1 μL of the matrix in the well. Since the CHCA matrix is solubilized in 1:1 ACN:0.1% TFA, both hydrophilic and hydrophobic peptide populations from the digest mixture should be resuspended with the low pH prohibiting any further CPY activity. The matrix crystal formation does not appear to be altered (as compared to the time-course experiment) by performing the digestion on-plate. This on-plate strategy significantly decreased the method optimization time by allowing multiple concentration-dependent (time-dependent) digestions to be performed in parallel. Also, sample losses upon transfer(s) from reaction vial to analysis plate were circumvented using the on-plate approach as all digested material is available for mass measurement.

Figure 4A:
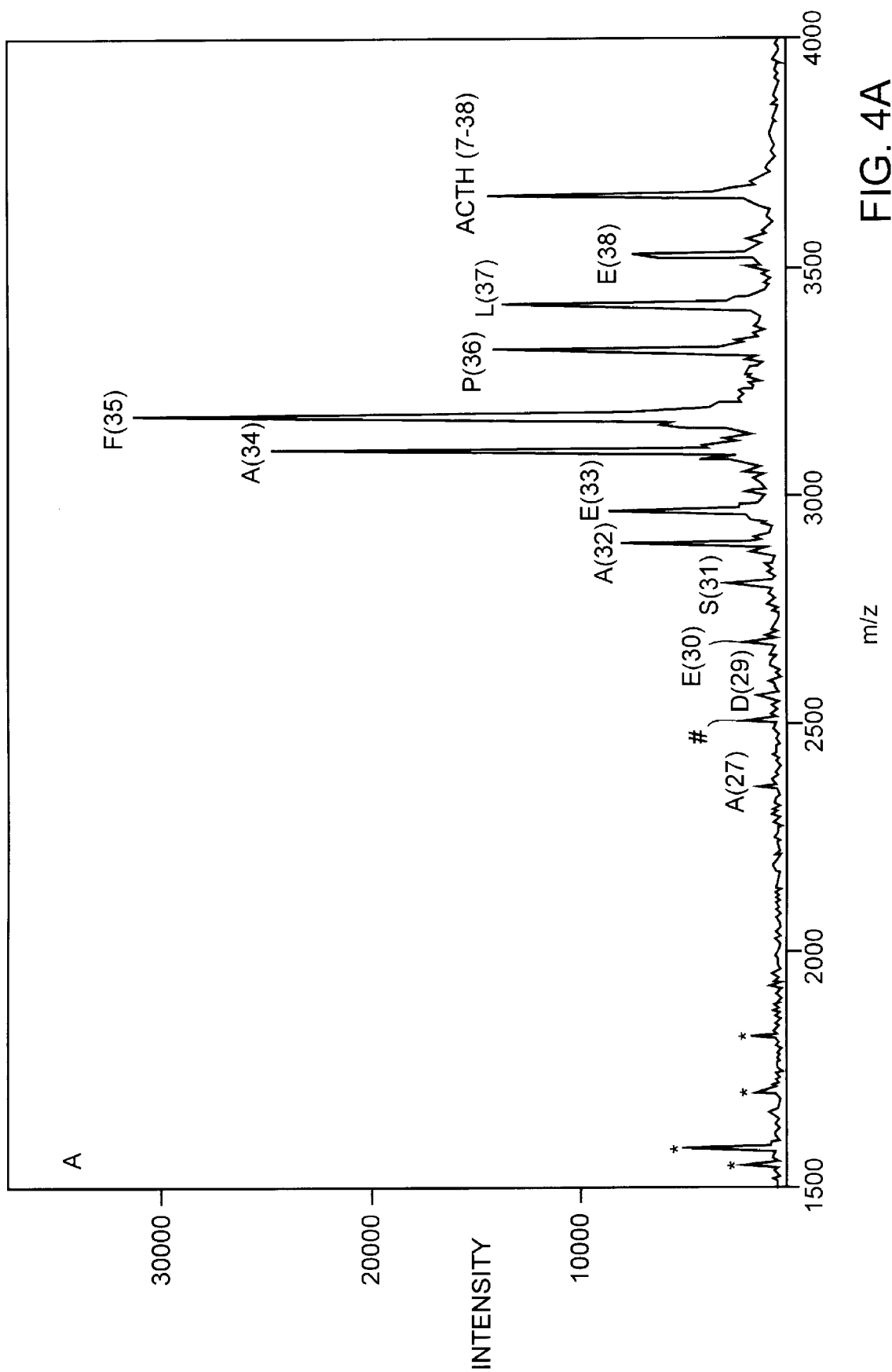
FIGS. 4A and 4B depict various MALDI spectra from on-plate digestions of ACTH 7–38 fragment concentrations of Carboxypeptidase Y (CPY): $6.10 \times 10^{-4}$ U/$\mu$l (4A); $1.53 \times 10^{-3}$ U/$\mu$l (4B).
Figure 4B:
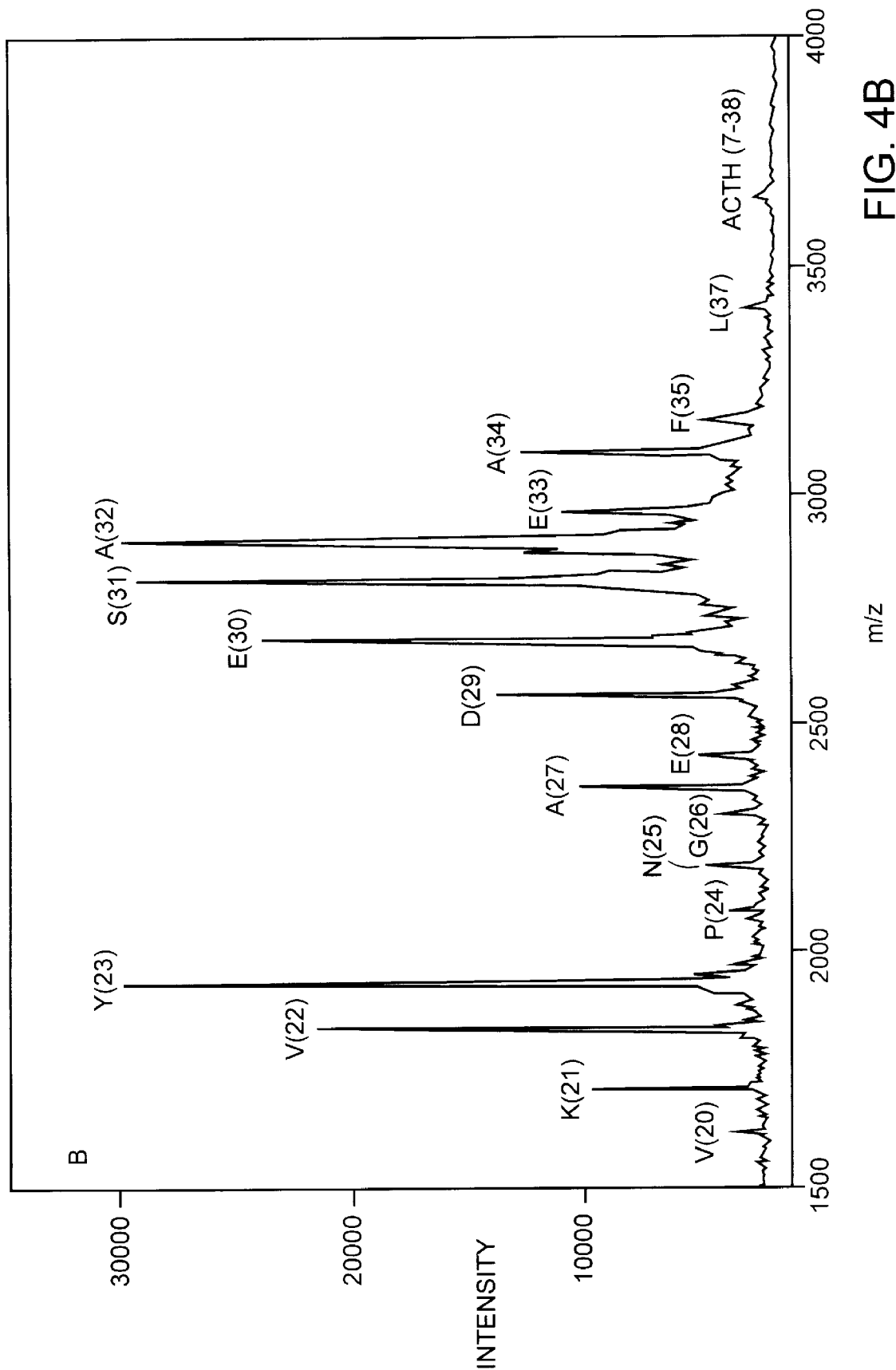

MALDI spectra corresponding to the on-plate concentration dependent digestions of the ACTH 7–38 fragment for CPY concentrations of $6.10 \times 10^{-4}$, and $1.53 \times 10^{-3}$ units/μL, respectively, are illustrated in panels A and B of FIG. 4. Panel A and B show the spectra obtained from digests using CPY concentrations of $6.10 \times 10^{-4}$ and $1.53 \times 10^{-3}$ units/μL, respectively. Laser powers significantly above threshold were used to improve the signal-to-noise ratio of the smaller peaks in the spectrum at the expense of peak resolution. The symbol * indicates doubly charged ions and # indicates an unidentified peak at m/z–2517.6 daltons.

The lower concentration digestion yielded 12 significant peaks representing the loss of 11 amino acids from the C-terminus. The digestion from the higher concentration of CPY showed some overlap of the peptide populations present at the lower concentration as well as peptide populations representing the loss of amino acids through the Val(20). The concentration of the peptides representing the loss of the first few amino acids have decreased to undetectable levels (approximately <10 fmol) with the exception of the Leu(37) peak. By integrating the information in both panels, the ACTH 7–38 fragment sequence can be read 19 amino acids from the C-terminus without gaps, stopping at the same amino acid run of peptide-RRKKP as the time-dependent digestion. FIG. 4 represents 2 of the 9 CPY concentrations that were performed simultaneously. The method optimization, in this case, was inherent in the strategy. The total time of method development (optimal digestion conditions), digestion, data collection and data analysis was under 30 min using this on-plate approach. The consumption of both peptide and enzyme was minimal as a total of 5 pmol of total peptide was digested across the 10 well row containing 9 digestions and 1 well with peptide plus water. Also, only 1.97 pmol of CPY (assuming 100 unit/mg and MW=61,000) was required for the entire experiment.

TABLE 1

| Peptide | SEQ ID Nos. | Sequence | Average Mass | Charge | Polarity |
| --- | --- | --- | --- | --- | --- |
| Sleep Inducing Peptide | 1 | Trp Ala Gly Gly Asp ALa Ser Gly Glu | 848.8 | <2.0 | polar |
| Amino Terminal Region of Hbs β chain[3] | 2 | Val Hrs Leu Thr Pre Val Glu Lys | 922.1 | +0.5 | mid |
| Interleukin-1β 163–171 Fragment[3] | 3 | Val Gln Gly Glu Glu Ser Asp Asp Lys | 1005.0 | −2.0 | polar |
| TRH Precursor | 4 | Lys Arg Gln His Pro Gly Lys Arg | 1006.2 | +4.5 | very |
| Bradykinin | 5 | Arg Pro Pro Gly Phe Ser Pro Phe Arg | 1061.2 | +2.0 | mid |
| Lutenizing Hormone Releasing Hormone[3] | 6 | pyro Glu His Trp Ser Tyr Gly Leu Ars Pro Gly amide | 1182.3 | +1.5 | mid |
| Physalaemin | 7 | pyro Glu Ala Asp Pro Asn Lys Phe Tyr Gly Lpo Mel amide | 1265.4 | 0 | mid |
| Angiotensin 1 | 8 | Asp Arg Val Tyr He His Pro Phe Hig Leu | 1295.5 | +1.0 | non |
| Renin Inhibitor | 9 | Pro Hic Pro Phe His Phe Pre Val Tyr Lys | 1318.5 | +2.0 | non |
| Kassinin | 10 | tsp Val Prole Ber Ase Gln Pre Val Gyl Leu Met | 1334.5 | −2.0 | non |
| Substance P | 11 | Arg Pre Lys Pro Glu Glyn Phe Phe Gly Leu Mgt | 1347.6 | +3.0 | mid |
| T-Antigen Homolog | 12 | Ays Pol Tp Gly Pro Lys Lys Lys Arg Lys Val Gly Gly | 1377.7 | +5.0 | polar |
| Osteocalcin 7–19 Fragment | 13 | Gly Ala Pro Val Pro Tyr Pro Asp Pro Leu Glu Pro Arg | 1407.6 | −1.0 | mid |
| Fibrinopeptide A | 14 | Ala Asp Ser Gly Glu Gly Asp Phe Leu Ala Glu Gly Gly Gly Val Arg | 1536.6 | −3.0 | mid |
| Thymopoietin II 29–41 Fragment | 15 | Gly Glh Glo Aerg Lys Asp Val Tyr Val Gln Leu Tyr Leu | 1610.8 | 0 | polar |
| Bombesin | 16 | pyro Glu Gln Arg Leu Gly Asn Gln Trp (Ala Val Gly His)Leu Met.amide | 1619.9 | +1.5 | mid |
| ACTH 11–24 Fragment | 17 | Lys Pro Val Gly Lys Ls Arg Arg Pro Bal Lys Val Tyr Pro | 1652.1 | +6.0 | mid |
| α-Melanocyte Stimulating Hormone | 18 | acetyl Set Thr Ser Met Gly His Phe Arg Trp Gly Lys Pro Val. amide | 1664.9 | +1.5 | mid |

TABLE 1-continued

| Peptide | SEQ ID Nos. | Sequence | Average Mass | Charge | Polarity |
|---|---|---|---|---|---|
| Angiotensinogen 1–14 Fragment | 19 | Asp Ars Val Tyr Ile His Pro Phe His Leu Leu Val Tr Ser | 1759.0 | +1.0 | non |
| Angiogenin | 20 | Glu Asn Gly Leu Pro Val His Leu Asp Lgn Ser Ile(Pre Arg) Arg | 1781.0 | +0.5 | mid |
| Glucagon | 21 | His Ser Gln Asp Ser Arg Arg Als Gln Asp Pre Val Gln Trp (Lau Net Asn) Thr | 3482.8 | +1.0 | polar |
| ACTH7-38 Fragment | 22 | Phe Arg Trp Gly Lys Pro Val Gly Lys Lys Arg Arg Pro Val Lys Val Tyr Pro Asn Gly Ala Glu Asp Glu Ser Ala Glu Ala Phe Pro Leu Glu | 3659.15 | +2.0 | polar |

[1]calculated
[2]at pH 6.5
[3]no sequence information was obtained

Listed in Table 1 are the peptides that have been digested and analyzed using this novel on-plate strategy. These peptides were selected to represent peptides of varying amino acid composition, size (up to MW=3659.15), charge and polarity. The bolded amino acids indicate that a peak representing the loss of that residue was observed in one or more of the MALDI spectra taken across the row of digestions. In order to be able to identify a residue, the peak representing the loss of that amino acid and the preceding amino acid must be present. The residues that are enclosed in parenthesis are those for which the sequence order could not be deduced. Overall, CPY offered some sequence information from the C-terminus for most of the peptides digested, lending no sequence information in only three of the 22 cases. In two of these three cases, the C-terminus was a lysine followed by an acidic residue at the penultimate position. CPY has been reported to possess reduced activity towards basic residues at the C-terminus, and the presence of the neighboring acidic residue seems to further reduce its activity. In the case of the lutenizing hormone releasing hormone (LH-RH), the C-terminal amidated glycine followed by proline at the penultimate position inhibited CPY activity which agrees with reports of CPY slowing at both proline and glycine residues (Hayashi et al. (1975) *J. Biochem.* 77:69–79; Hayashi, R. (1976) *Methods Enzymol.* 45:568–587). CPY is known to hydrolyze amidated C-terminal residues of dipeptides and is shown here to cleave those of physalaemin, kassinin, subtance P, bomesin, and α-MSH.

As illustrated by the data in Table 1, CPY was able to derive sequence information from all of the peptides, except LH-RH, that possess blocked N-terminal residues (physalaemin, bombesin and α-MSH). This is significant as these peptides would lend no information to the Edman approach. A number of the peptides were sequenced until the detection of the truncated peptide peaks were impaired by the presence of CHCA matrix ions (<600 daltons). The sequencing of the other peptides did not go as far as a combination of residues at the C-terminus and penultimate position that inhibited CPY activity were encountered. Bombesin, angiogenin and glucagon gave gaps in the sequence as residues that were cleaved slowly were followed by residues hydrolyzed more rapidly, as discussed above. The feasibility of the on-plate CPY digestion/MALDI detection strategy appeared to be independent of the overall polarity and charge of the peptide.

Figure 5A:
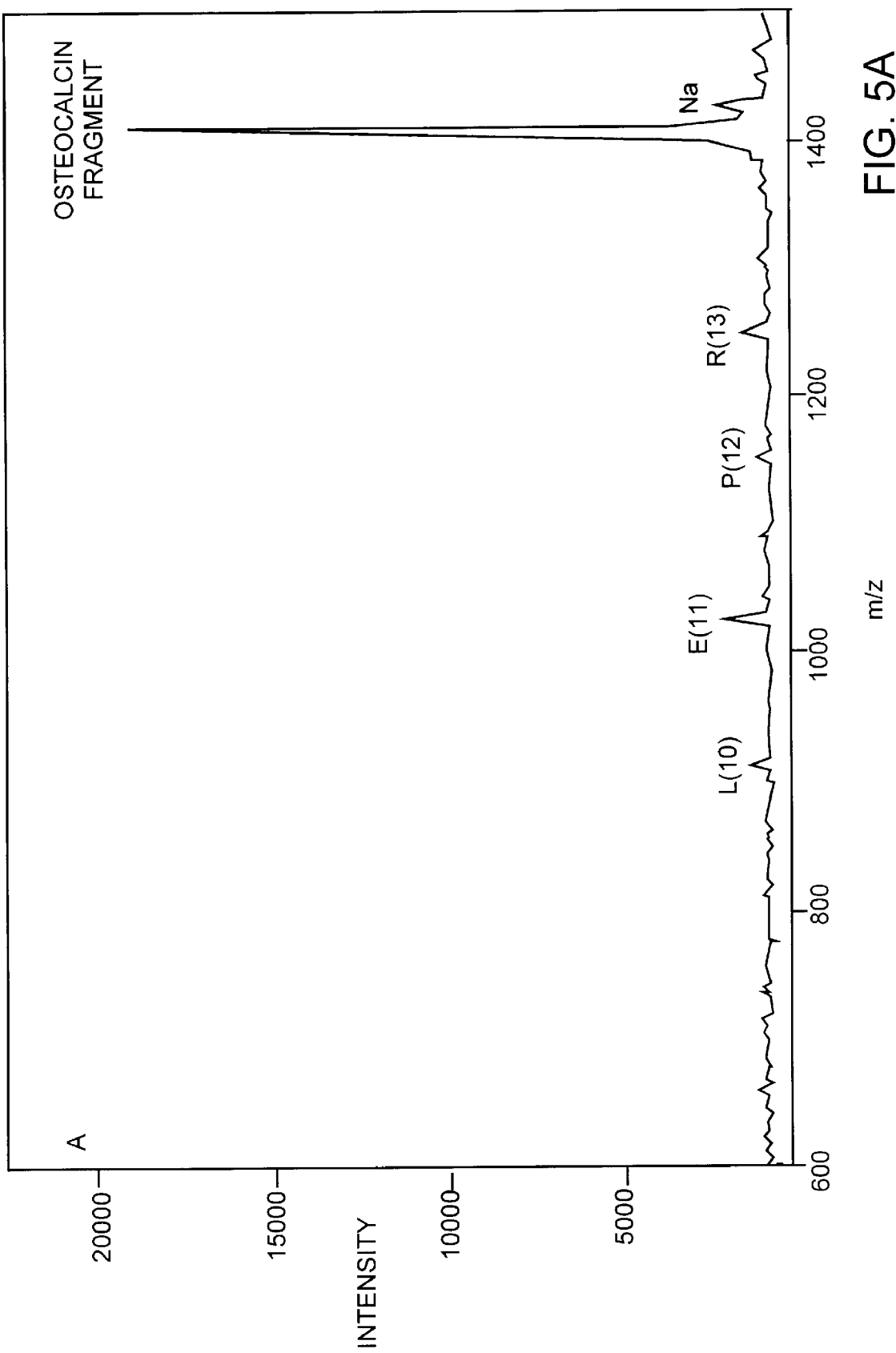
FIGS. 5A, 5B, and 5C depict various MALDI spectra of the following three selected peptides, osteocalcin 7–19 fragment [GlyAlaProValProTyrProAspProLeuGluProArg], SEQ. ID. No: 13 (5A) angiotensin 1 [AspArgValTyrIleHisProPheIlsLeu], SEQ. ID. No: 8 (5B) and bradykinin [ArgProProGlyPheSerProPheArg], (SEQ. ID. No: 5)(5C).
Figure 5B:
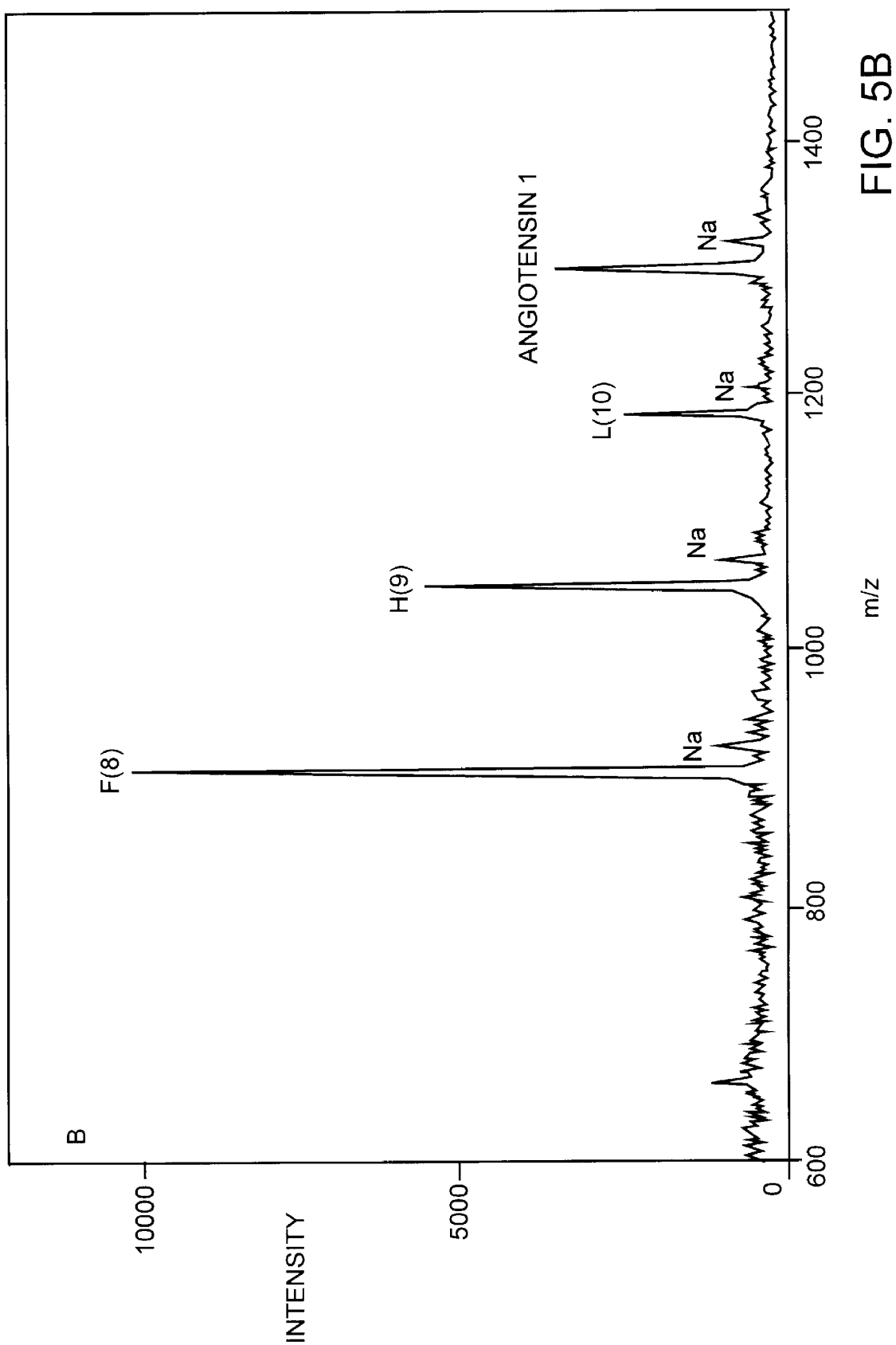
Figure 5C:
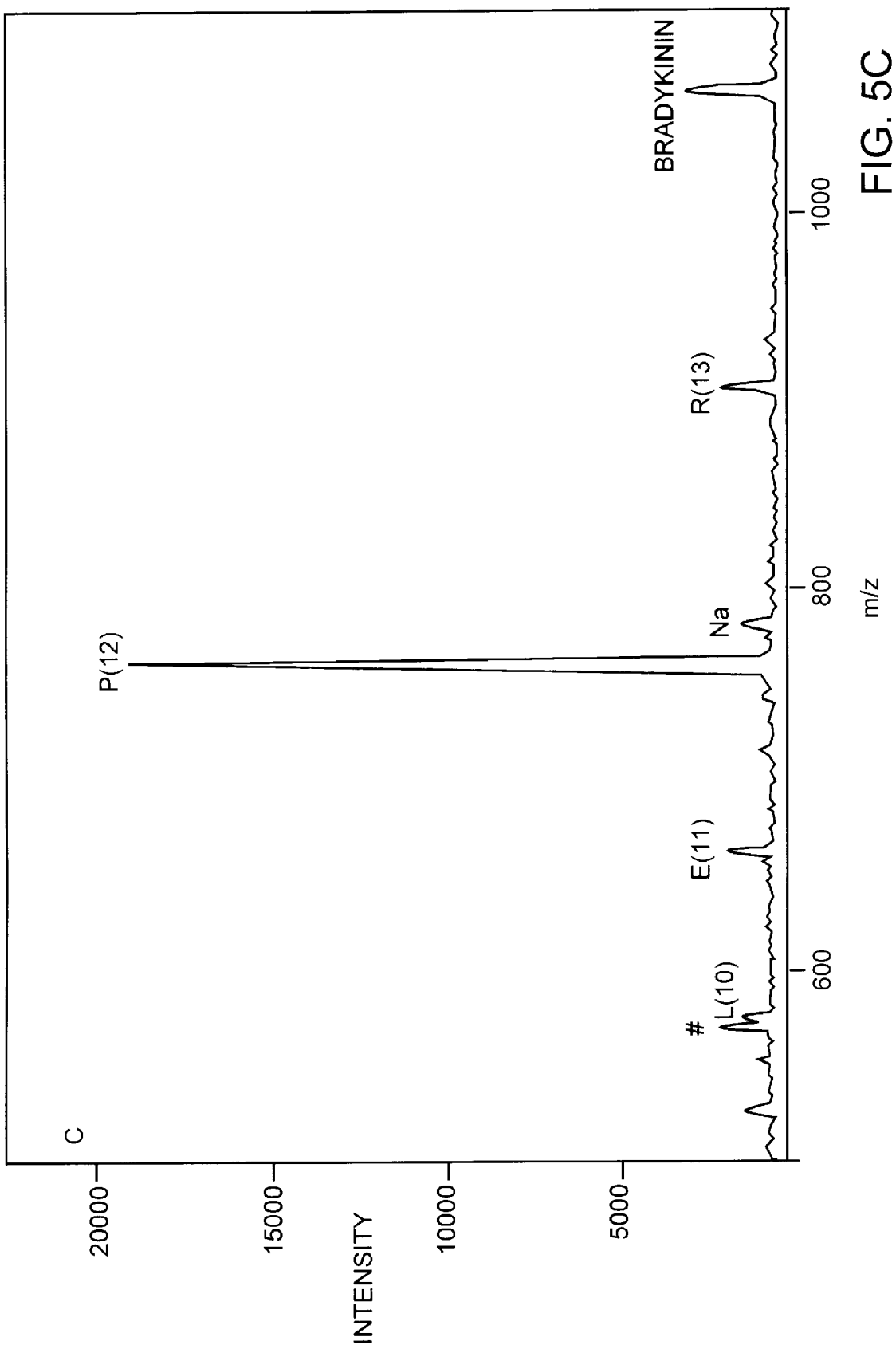
Figure 6A:
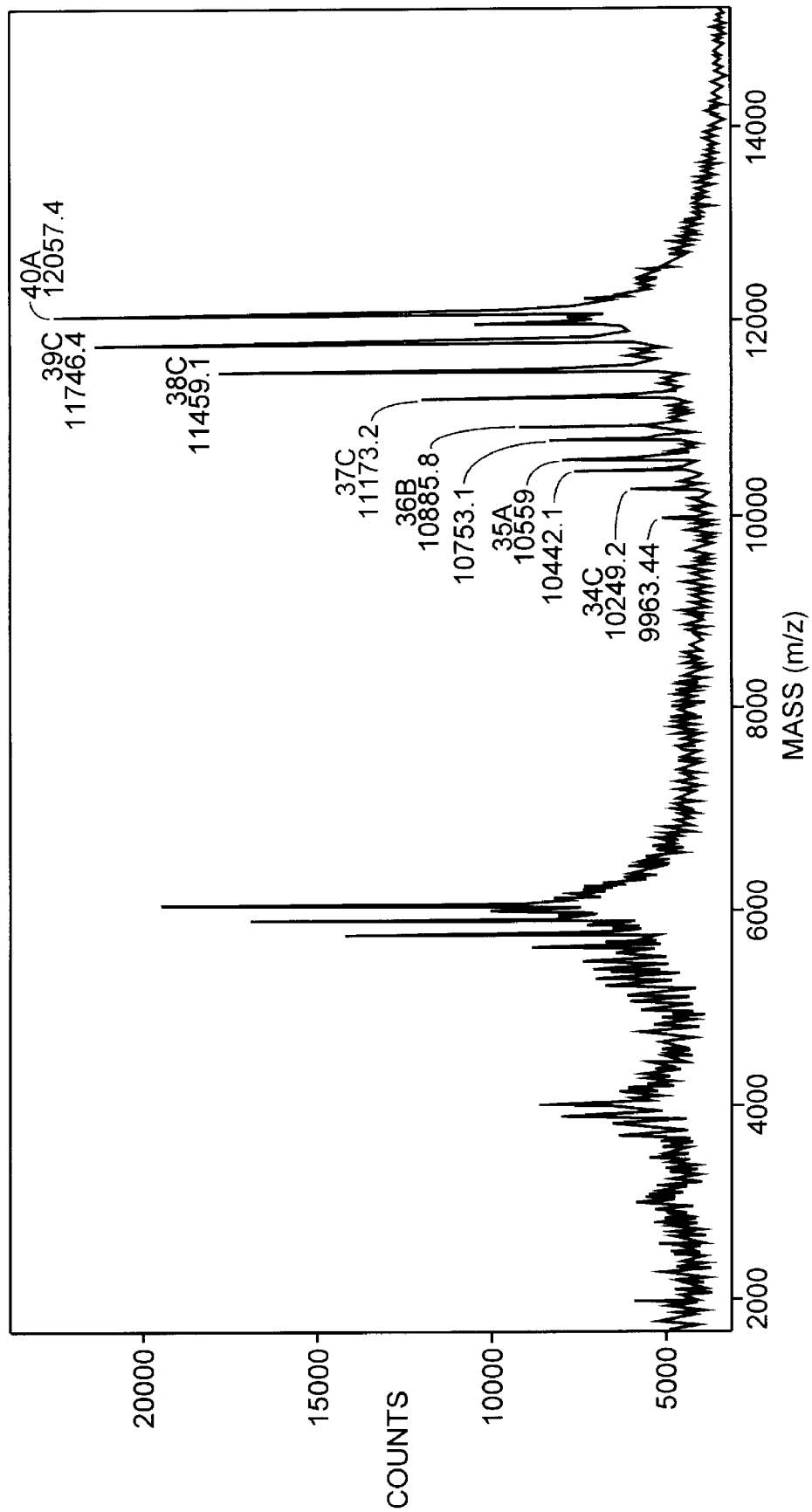
FIGS. 6A–6E depict various MALDI spectra of exonuclease hydrolysis of a nucleic acid polymer (SEQ. ID. No. 23) at various concentrations of Phosphodiesterase I (Phos I): 0.002 $\mu$U/$\mu$l (6A); 0.005 $\mu$U/$\mu$l (6B); 0.01 $\mu$U/$\mu$l (6C); 0.02 $\mu$U/$\mu$l (6D); 0.05 $\mu$U/$\mu$l (6E).
Figure 6B:
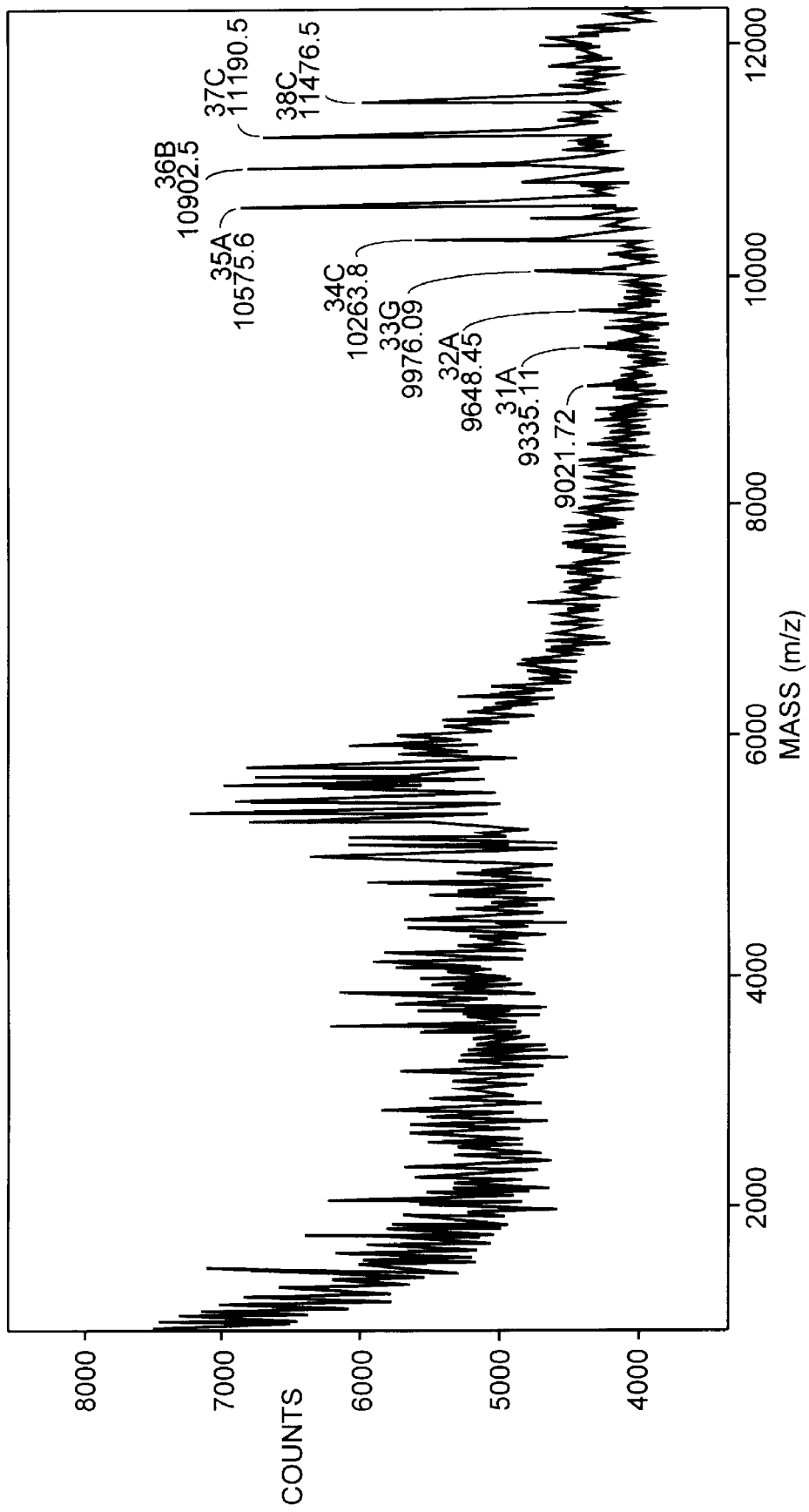
Figure 6C:
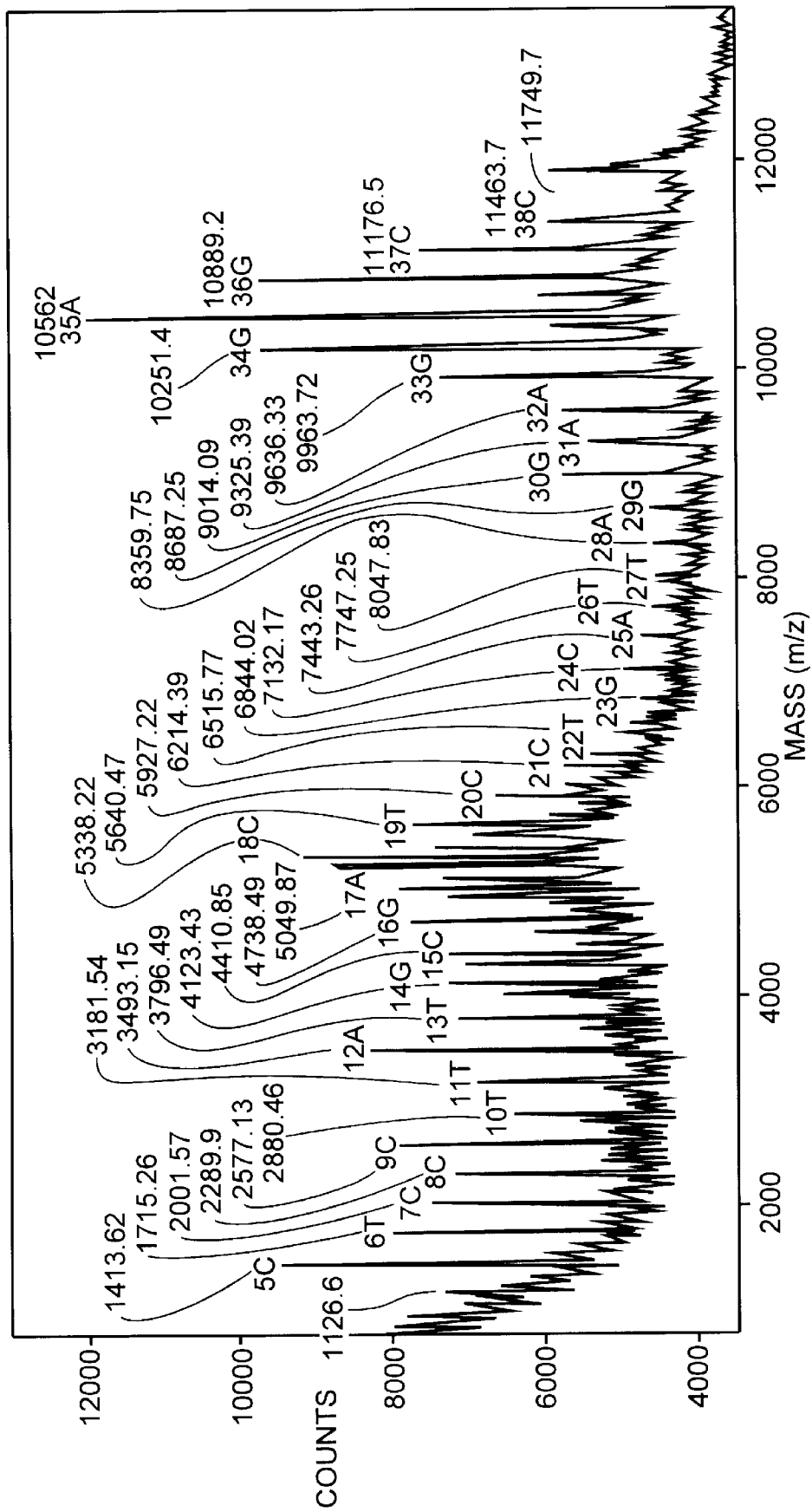
Figure 6D:
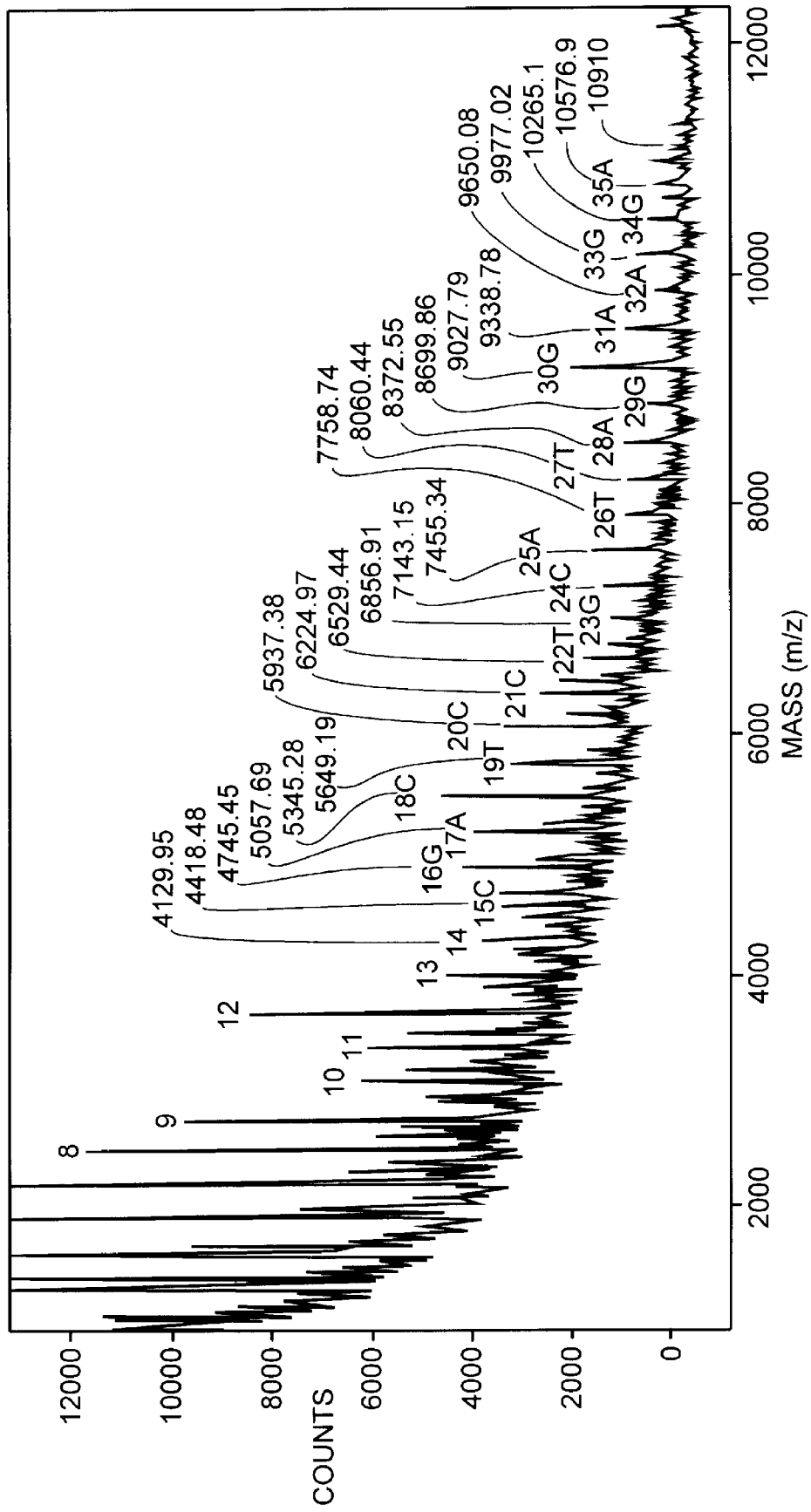
Figure 6E:
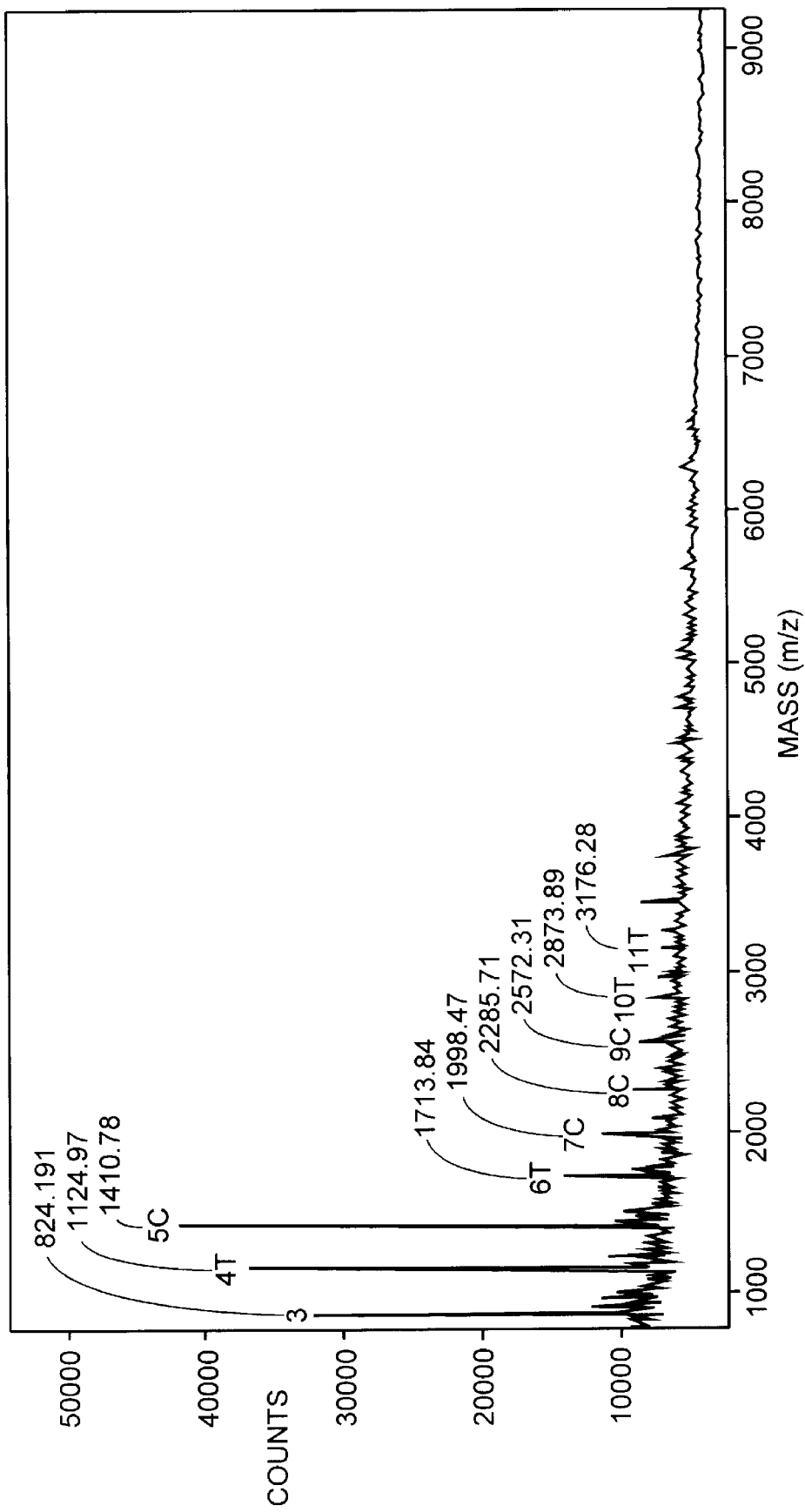

FIG. 5 shows selected on-plate digestions of osteocalin 7–19 fragment, angiotensin 1 and bradykinin resulting from on-plate digestions using CPY concentrations of $3.05 \times 10^{-3}$, $3.05 \times 10^{-4}$, and $6.10 \times 10^{-4}$ units/µL, respectively. The symbol Na denotes a sodium adduct peak and # denotes a matrix peak at m/z–568.5 daltons.

Each spectrum represents the results of one of the 9 digestions that was performed across the row of wells. In the case of the osteocalcin 7–19 fragment, CPY can proceed through proline (Martin, B. (1977) *Carlsbura Res. Commun.* 42:99–102; Breddam et al. (1987) *Carlsbura Res. Commun.* 52:55–63; Breddam, K. (1986), *Carlsburg Res. Commun.* 51:83–128; Hayashi, R. (1977) *Methods Enzymol.* 74:84–94; Hayashi et al. (1973) *J Biolog. Chem.* 248:2296–2302); the presence of Asp and His at the respective penultimate positions of the two peptides prohibited further CPY activity. Bradykinin is shown to sequence until the matrix begins to interfere with peak detection. For all three of the selected peptides, the total sequence information obtained for the overall 9 well digestion is represented in the single digestion shown. For many other peptides this was not the case. The total sequence information is often derived from 2 or more of the wells as is the case with ACTH 7–38 fragment given in FIG. 4.

EXAMPLE 3. STATISTICAL ANALYSIS OF LADDER SEQUENCING BY MALDI (a) General Principles of Statistical Analysis According to the Instant Invention As disclosed above, once the truncated ladders have been formed, matrix is added to the well and multiple measurements were taken from the wells in which peaks representing the loss of an amino acid(s) are present. Statistical interpretation involving the use of t-statistics then allowed assignments to be made with an associated confidence interval. The two-tailed test for one experimental mean, $$t_{calculated} = \frac{|x - \mu| \sqrt{N}}{S}$$

where x is the experimental mean mass difference, $\mu$ is the asserted mass difference, N is the number of replicates performed, and S is the experimental standard deviation of the mean, was applied. All conceivable masses (single residue, di-residue, tri-residue, etc., as well as modified residue masses) were used as $\mu$, the asserted mass, to generate a list of $t_{calculated}$ values that were then compared against tabulated values for given confidence intervals. All masses that did not statistically differ from the asserted mass, $t_{calculated} < t_{table}$ were statistically assigned to that residue(s) at the given level of confidence. This information was used to check hypothesized composition or used to search a database for a sequence. When performing database searching, these levels of confidence can be used in the search algorithm as a tool to aid in obtaining quality "hits."

Additionally, the interpretation of data utilized an automated process of acquiring and interpreting the data using software feedback control. The data interpretation software controls the number of acquisitions (minimum of 2) that are required to statistically differentiate multiple candidates for an amino acid assignment. The operator has control of specifying to what minimum statistical level of confidence the assignment(s) should meet.

(b) Analysis of Experimentally-Obtained Mass-to-Charge Ratio Data: Peptides

The use of MALDI for the analysis of truncated ladders as disclosed herein is critical for obtaining accurate sequence data. In the prior art, the technique has been used almost exclusively to sequence peptides of a defined sequence for which the mass accuracy of the measurement is of little importance. In contrast, the methods disclosed herein are useful for the sequence determination of peptides of unknown sequence. By comparing known molecular masses to the MALDI derived masses for only a few mass measurements, artisans previously have made only general statements of instrumental mass accuracy (e.g., better than 0.1%), but, ascribing this mass accuracy to any individual mass measurement for the purpose of residue assignment holds no statistical validity. Therefore, true residue assignment and direct application to unknowns has heretofore been both difficult and tentative. In order to derive amino acid sequences by ladder sequencing/MALDI strategies, statistical levels of confidence must be placed on residue assignments as disclosed herein.

To place confidence levels on residue assignments, the nature of the experimental errors first must be defined. For systems in which the errors are random, simple t-statistics can be used for amino acid assignment.

To assess the nature of the errors that dominate MALDI analysis of the above-described truncated peptide ladders, the Δ mass differences (i.e., experimental mass difference—actual amino acid mass) for all amino acid assignments made in the 15 aliquots (one spectrum per aliquot) removed from the time-dependent digestion of ACTH 7–38 fragment described above were measured to yield a gaussian distribution with a mean of 0.0089±0.605 (n=107). For this experiment $t_{calculated}$ (0.152)<$t_{table}$ (1.99) indicating that the null hypothesis that the average Δ mass difference=0 cannot be rejected at a 95% confidence level. This indicates that the error is random with no statistically significant systematic error. This is expected as any systematic errors that are present in the mass assignment of individual peptide peaks such as incorrect y-intercept values for two-point mass calibration should cancel out when calculating the mass difference of two adjacent peaks. There are possible systematic components of error that would not be canceled such as incorrect computation of the mass center of one of a set of two adjacent peaks due to partial resolution of the isotopes. This phenomenon was circumvented by the use of a smoothing filter such that all peaks were detected at the actual average mass values.

TABLE 2

| Amino Acid (position) | Actual Mass[1] | Experimental Mass[1,2] | Replicates |
| --- | --- | --- | --- |
| val(20) | 99.13 | 98.97 ± 0.52 (1.29) | 3 |
| lys(21) | 128.17 | 128.15 ± 0.48 (0.44) | 7 |
| val(22) | 99.13 | 99.20 ± 0.35 (0.27) | 9 |
| tyr(23) | 163.17 | 162.43 ± 0.11 (0.99) | 2 |
| pro(24) | 97.12 | 97.49 ± 0.14 (1.25) | 2 |
| asn(25) | 114.10 | 114.21 ± 0.82 (0.69) | 8 |
| gly(26) | 57.05 | 57.22 ± 0.88 (0.68) | 9 |
| ala(27) | 71.07 | 70.19 ± 0.49 (4.40) | 2 |
| glu(28) | 129.12 | 130.22 ± 0.47 (4.22) | 2 |

TABLE 2-continued

| Amino Acid (position) | Actual Mass[1] | Experimental Mass[1,2] | Replicates |
| --- | --- | --- | --- |
| asp(29) | 115.09 | 114.81 ± 0.58 (0.41) | 10 |
| glu(30) | 129.12 | 129.27 ± 0.61 (0.39) | 12 |
| ser(31) | 87.08 | 87.14 ± 0.47 (0.30) | 12 |
| ala(32) | 71.07 | 80.94 ± 0.49 (0.51) | 6 |
| glu(33) | 129.12 | 129.39 ± 0.42 (0.44) | 6 |
| ala(34) | 71.07 | 71.09 ± 0.30 (0.28) | 7 |
| phe(35) | 147.18 | 147.03 ± .73 (0.77) | 6 |
| pro(36) | 97.12 | 96.83 ± 0.64 (1.18) | 4 |
| leu(37) | 113.16 | 113.63 ± 0.54 (1.34) | 3 |
| glu(38) | 129.12 | 128.40 ± 0.52 (1.29) | 3 |

[1] the masses given are average masses and in units of daltons
[2] the uncertainties of the experimental mass measurements are given as standard deviations (those in the parenthesis are 95% confidence intervals of the mean)

Table 2 represents a comparison of the actual average masses of the sequenced residues of the ACTH 7–38 fragment and the experimental mass differences with associated standard deviations and 95% confidence intervals calculated for the time-dependent digestion. The number of replicates indicate the number of spectra that possessed the detectable adjacent peaks required for the mass difference measurement of that particular residue. The need for a significant number of measurements in order to estimate the mean is obvious from the table as the 95% confidence level decreases as the square root of the number of measurements. For all of the residues sequenced, the actual mass fell within ±3σ the experimental mass distribution. Calculated t-values for each case were less than the tabulated t-value for the 95% confidence interval signifying that the experimental mass is not significantly different than the actual known mass. In order to statistically assign the residues, a calculated t-value for each possible amino acid must be compared with the tabulated value. In other words, the actual masses of all possible amino acids must be used as an asserted mean, $\mu$, and each null hypothesis (i.e., $\bar{x}-\mu=0$) made such that a calculated t-value for each possible assignment can be compared to the tabulated value.

Assuming that only the 20 common unmodified amino acids are possible, this was done for the prior art time-dependent ACTH 7–38 fragment digestion. A summary of the results is given in Table 3. The bolded values are those which the experimental mean did not significantly differ from the asserted amino acid mean. Again, the need for adequate population sampling is apparent. There were only two measurements observed for the Glu(28) thereby resulting in a 95% confidence interval of 4.22 daltons (Table 2). This translates into an inability to distinguish between Gln, Lys, Glu and Met (Table 3). The 12 trials that were observed for Glu(30) gave a 95% confidence interval of 0.39 daltons, thereby rendering the Gln, Lys and Met statistically improbable amino acid assignments.

Table 3 represents calculated t-values for 19 sequenced amino acid experimental means in the ACTH 7–38 fragment given the asserted means of 20 common unmodified amino acids. The $t_{table}$ value is given at the end of each column. A $t_{calculated} < t_{table}$ indicates that the experimental mean is not significantly different that the mean of the asserted amino acid at 95% confidence interval. Each $t_{calculated}$ for which this is the case is indicated in bold.

TABLE 3

| | ACTH 7–38 Fragment Amino Acid Position | | | | | | | | | | | | | | | | | | |
|---|---|---|---|---|---|---|---|---|---|---|---|---|---|---|---|---|---|---|---|
| | 20 | 21 | 22 | 23 | 24 | 25 | 26 | 27 | 28 | 29 | 30 | 31 | 32 | 33 | 34 | 35 | 36 | 37 | 38 |
| Gly | | | | | | 0.58 | 37.9 | | | | | | 69.4 | | 123 | | | | |
| Ala | | | | | | 47.2 | 2.54 | | | | | 118 | 0.65 | | 0.18 | | | | |
| Ser | | | | 105 | | 48.7 | | | | | | 0.44 | 80.7 | | 141 | | 30.5 | | |
| Pro | 6.16 | | 17.8 | 3.74 | | | | | | | | 73.6 | | | | | 0.91 | | |
| Val | 0.53 | | 0.60 | 16.6 | | | | | | | | | | | | | 7.19 | | |
| Thr | 7.09 | | 16.3 | | | | | | | | | | | | | | | | |
| Cys | | | | | | | | | | | | | | | | | 33.6 | | |
| Leu/Ile | | | | 3.62 | | | | | | | | | | | | | 1.51 | | |
| Asn | | | | 0.38 | | | | | 3.87 | | | | | | | | 1.51 | | |
| Asp | | 72.0 | | | 3.04 | | | | 45.5 | 1.53 | | | | | | | | 4.68 | 44.3 |
| Gln | | 0.11 | | | | | | | 6.29 | 72.6 | | | | | | | | | 0.90 |
| Lys | | 0.11 | | | | | | | 6.17 | | 6.25 | | | 7.12 | | | | | 0.77 |
| Glu | | 5.35 | | | | | | | 3.31 | | 0.85 | | | 1.57 | | | | | 2.40 |
| Met | | | | | | | | | 2.95 | | 11.0 | | | 10.6 | | | | | 9.33 |
| His | | | | | | | | | 20.8 | | | | | | | 33.2 | | | |
| Phe | | | | | | | | | | | | | | | 0.50 | | | | |
| Arg | | | | 80.4 | | | | | | | | | | | | | 30.7 | | |
| Tyr | | | | 9.64 | | | | | | | | | | | | | | | |
| Trp | | | | 305 | | | | | | | | | | | | | | | |
| 'table' | 4.30 | 2.45 | 2.31 | 12.7 | 12.7 | 2.37 | 2.31 | 12.7 | 12.7 | 2.26 | 2.20 | 2.20 | 2.57 | 2.57 | 2.45 | 2.57 | 3.18 | 4.30 | 4.30 |

[1]the tabulated t value associated with an area of 0.025 in one tail of the t-distribution corresponding to the appropriate degrees of freedom, $v$, where $v = n - 1$.

Table 4 summarizes the results of the statistical amino acid assignments for the 19 amino acids sequenced from the C-terminus of ACTH 7–38 fragment using the prior art time-dependent strategy. The masses of the listed amino acids could not be statistically differentiated from the experimentally derived mass difference at the given confidence levels. The amino acids indicated in bold are the known residues existing at the given positions. The confidence intervals indicared are the highest levels at which all amino acid masses other than those indicated are statistically different from the experimental mean.

daltons). The same phenomenon occurred in the assignment of residue 37. The experimental mean (113.63 daltons) bisected the asserted means of Leu(Ile) (113.16 daltons) and Asn (114.10 daltons). The assignments of the amino acids at positions 28 and 38 were difficult due to the small number of replicates taken (2 and 3, respectively). Residue 28 was assigned Gln/Lys/Glu/Met at a confidence interval greater than 95% but less than 98%. Table 3 shows that, for this residue, the asserted amino acid mass that resulted in the smallest $t_{calculated}$ was that of methionine. Using a confidence interval of 80%, the correct assignment of Glu is

TABLE 4

| ACTH 7–38 Fragment Amino Acid Position | Amino Acid Assignments[1] | Confidence Interval (c.i.) |
|---|---|---|
| 20 | Val | 95% < c.i < 98% |
| 21 | Gln/Lys | c.i. > 99.8% |
| 22 | Val | c.i. > 99.8% |
| 23 | Tyr | 99% < c.i. < 99.8% |
| 24 | Pro | 95% < c.i. < 98% |
| 25 | Asn | 98% < c.i. < 99% |
| 26 | Gly | c.i. > 99.8% |
| 27 | Ala | 98% < c.i. < 99% |
| 28 | Gln/Lys/Glu/Met | 95% < c.i. < 98% |
| 28 | Met | 80% < c.i. < 90% |
| 29 | Asp | 99% < c.i. < 99.8% |
| 30 | Glu | c.i. > 99.8% |
| 31 | Ser | c.i. > 99.8% |
| 32 | Ala | c.i. > 99.8% |
| 33 | Glu | c.i. > 99.8% |
| 34 | Ala | c.i. > 99.8% |
| 35 | Phe | c.i. > 99.8% |
| 36 | Pro | 99% < c.i. < 99.8% |
| 37 | Leu(Ile)/Asn | 95% < c.i. < 98% |
| 38 | Gln/Lys/Glu | 98% < c.i. < 99% |
| 38 | Gln/Lys | 80% < c.i. < 90% |

[1]assuming that only the 20 common unmodified amino acids are probable candidates For example, the distinction between Gln and Lys for the amino acid assignment of residue 21 could not be made as the experimental mean (128.15 daltons) exactly bisected the asserted means of Gln (128.13 daltons) and Lys (128.17 deemed statistically improbable. Likewise, the assignment of residue 38 was made as Gln/Lys/Glu at a confidence level of 95%, but the correct assignment (Glu) is again statistically improbable at an 80% level.

Since the errors are randomly distributed, all amino acids can be differentiated (except Leu and Ile) by sufficient population sampling. Approximating the experimental standard deviation to be that given above of s=0.604 for the overall experiment, it is approximated (using $t_{table}$=1.960) that >876 measurements would be required to differentiate Gln and Lys (Δ mass=0.04 daltons) at a 95% confidence interval. This number is experimentally impractical, but can be significantly lowered by reducing the standard deviation of the experimental mean. Decreasing the experimental standard deviation is of significant value as the number of samples required for the distinction between two amino acids to be made is proportional to the square of the experimental standard deviation of the mass difference. It is anticipated that mass shift reagents used to move peptide populations out of the interfering matrix are a possible chemical means for improving experimental error relating to peptides appearing in the low mass (<600 daltons) region. The use of reflectron and/or extended flight tube geometries are also expected to be instrumental methods suitable for reducing this error.

The protocol disclosed herein for statistical assignment of residues using the on-plate strategy involves multiple sampling from each well in which digestion is performed. The number of replicates required depends on the amino acid(s) that is(are) being sequenced at any one CPY concentration. For example, more replicates are required for mass differences around 113–115 daltons (Ile/Leu, Asn and Asp) and 128–129 daltons (Gln/Lys/Glu) than for mass differences around 163 (Tyr) or 57 (Gly) in order to be able to assure that all but one assignment are statistically unlikely. The experimental errors for this method appear to be as random (multiple replicates per sample) as for the time-dependent digestion (one replicate per sample).

This general statistical protocol for residue assignment was applied to two adjacent peaks that represent the loss of two or more amino acids. In this case, the asserted means of all dipeptides, tripeptides, etc. can also be used to calculate t-values. The information concerning the order of the residues will be lost but the composition can be deduced. Using only single amino acid and dipeptide masses as asserted means this was done for angiogenin has a sequence gap of Phe-Arg (Table 1). The average experimental mass difference between the peaks representing the loss of Arg(15) and Phe(13) was 303.45±0.328 (n=5). For all single amino acid and dipeptide masses except Phe/Arg, the calculated t-values are greater than the tabulated t-value at a confidence interval of 99.8%. In this particular case, the identity of the amino acids that comprise the gap was determined, but their order remains experimentally unknown. This statistical strategy was also incorporated into a computer algorithm to perform interactive data analysis and interpretation of ladder sequencing/MALDI experiments.

Thus, as illustrated above, the use of CPY digestion coupled with MALDI detection as disclosed herein was effective for obtaining C-terminal sequence information. The ACTH 7–38 fragment yielded sequence information 19 amino acids from the C-terminus without gaps. The on-plate concentration-dependent approach was demonstrated as a useful method for performing multiple digestions in parallel which circumvented the need for time- and reagent-consuming method development. This on-plate strategy required less physical manipulations and less total amounts of enzyme and peptide. Of the 22 peptides attempted using the on-plate approach, all but three were successfully digested to yield some C-terminal sequence information. CPY was also shown to cleave amidated C-terminal residues, but possessed no activity towards certain combinations of residues existing at the C-terminus and penultimate position.

In summary, an integrated strategy for generating residue assignments from "on-plate" C- and N-terminal peptide ladder sequencing experiments was developed. This strategy is based on the logical combination of tasks involving:

1) the creation of peptide ladders from a concentration-dependent exopeptidase digestion strategy that utilizes the μL-wells of the Voyager™ sample plate as microreaction vessels;

2) the use of the Voyager™ MALDI-TOF workstation as a tool to generate masses of the peptide fragment;

3) an interpretation algorithm based on t-statistics that allows elimination of asserted assignment candidates; and, 4) feedback control of the data acquisition software from the interpretation algorithm that governs the number of replicates that are acquired for the statistically-based assignments to be made completely or to a cost effective partial point.

(c) Analysis of Experimentally-Obtained Mass-to-Charge Ratio Data: Nucleic Acids The method disclosed herein has also been used to obtain sequence information about a nucleic acid polymer containing 40 bases. Hydrolysis using an exonuclease specific for the 3' terminus was conducted using different concentrations of Phos I (phosphodiesterase I) ranging from 0.002 μU/μl to 0.05 μU/μl. Hydrolysis was allowed to proceed for 3 minutes. Spectra of hydrolyzed sequences using MALDI-TOF are depicted in FIGS. 6A–6E. Data integration as disclosed herein confirmed the sequence to be:

CGC TCT CCC TTA TGC GAC TCC TGC ATT AGG AAG CAG CCC A SEQ. ID. No: 23

Figure 7:
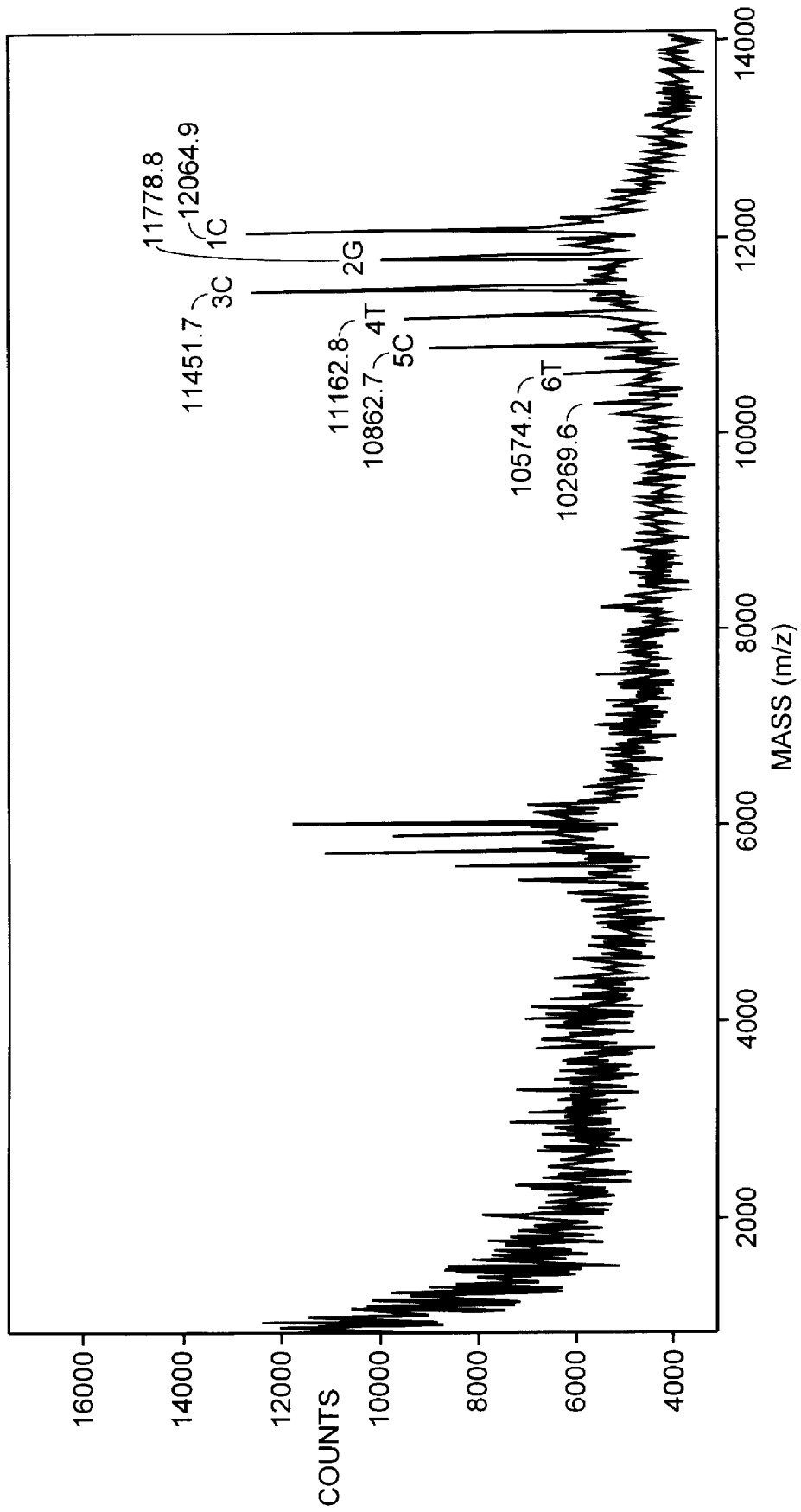
FIG. 7 depicts a MALDI spectrum of a hydrolyzed nucleic acid polymer (SEQ. ID. No. 23)combined with a light-absorbent matrix.

In a separate experiment, addition of a light-absorbent matrix CHCA was evaluated. A nucleic acid polymer containing 40 bases (as described above) was mixed with matrix and 0.4 μU/μl of the exonuclease Phos II (phosphodiesterase II) which is specific for the 5' terminus. Hydrolysis in the presence of matrix was allowed to proceed for 10 minutes. The spectrum obtained by MALDI-TOF is depicted in FIG. 7. These data confirm the ability to combine polymer, hydrolyzing agent and matrix prior to mass spectrometry analysis. This reduces handling of reagents and facilitates sample processing. Using data similar to those in FIG. 7, the sequence of the nucleic acid polymer was confirmed to be as described above.

EXAMPLE 4. OTHER APPLICATIONS OF THE INSTANT METHOD

As disclosed herein, this strategy can be applied to the sequencing of any natural biopolymer such as proteins, peptides, nucleic acids, carbohydrates, and modified versions thereof. The ladders can be created enzymatically using exohydrolases, endohydrolases or the Sanger method and/or chemically by truncation synthesis or failure sequencing.

It is expected that other approaches can be taken to expand the utility of the CPY/MALDI ladder sequencing methods disclosed herein. For example, by taking advantage of different enzyme specificities, the use of carboxypeptidase mixtures can be implemented using the disclosed on-plate strategy as a means for sequencing through residue combinations that prohibit CPY activity as well as preventing sequence gaps from occurring. Also, by covalently attaching N-terminal and/or C-terminal linkers to small peptides, it is expected that all sequence peaks can be made to fall beyond the low mass matrix region. It is anticipated that peptides can be completely sequenced to the N-terminus without gaps by combining MALDI with the above-described carboxypeptidase mixtures and mass shift reagent modifications.

Equivalents

The invention may be embodied in other specific forms without departing from the spirit or essential characteristics thereof. The foregoing embodiments are therefore to be considered in a all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A sample holder adapted to receive a polymer comprising a series of different monomers whose sequence is to be determined in a mass spectrometry apparatus, comprising a planar solid surface having at least two discrete spatial areas arrayed upon said planar solid surface and differing amounts of an agent capable of hydrolyzing a polymer disposed on each of said discrete spatial areas to form at least two discrete spatial areas wherein, upon the addition of said polymer, differing ratios of agent to polymer are formed in each of said discrete spatial areas, wherein said holder can be used to adapt said apparatus for obtaining sequence information about said polymer.

2. The sample holder of claim 1 wherein said agent capable of hydrolyzing a polymer comprises an immobilized agent disposed on each of said discrete spatial areas wherein, upon the addition of said polymer, differing ratios of agent to polymer are formed in each of said discrete spatial areas.

3. The sample holder of claim 1 wherein said agent capable of hydrolyzing a polymer comprises an agent in liquid or gel form, said liquid or gel form being resistant to physical dislocation, said agent disposed on each of said discrete spatial areas wherein, upon the addition of said polymer, differing ratios of agent to polymer are formed in each of said discrete spatial areas.

4. The sample holder of claim 1 wherein said agent capable of hydrolyzing a polymer is dehydrated.

5. A sample holder adapted to receive a polymer comprising a series of different monomers whose sequence is to be determined in a mass spectrometry apparatus, comprising a planar solid surface having at least two discrete spatial areas arrayed upon said planar solid surface, a polymer, and at least one amount of an agent capable of hydrolyzing a polymer on each of said discrete spatial areas to form at least two discrete spatial areas wherein, upon the addition of said polymer, differing ratios of agent to polymer are formed in each of said discrete spatial areas, wherein said holder can be used to adapt said apparatus for obtaining sequence information about said polymer.

6. The sample holder of claim 1, 2, 3 or 5 wherein continuously increasing amounts of said agent are disposed on each of said discrete spatial areas.

7. The sample holder of claim 1, 2, 3 or 5 further comprising a light-absorbent matrix disposed on at least one of said discrete spatial areas.

8. The sample holder of claim 1, 2, 3 or 5 wherein said discrete spatial areas are wells or chambers.

9. The sample holder of claim 1, 2, 3 or 5 wherein said holder is made of material selected from the group consisting of metals, foils, plastics, ceramics and waxes.

10. The sample holder of claim 5 wherein said agent is present in constant or differing amounts.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Trp  Ala  Gly  Gly  Asp  Ala  Ser  Gly  Glu
    1                           5

( 2 ) INFORMATION FOR SEQ ID NO:2:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Val  His  Leu  Thr  Pro  Val  Glu  Lys
    1                         5

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

Val  Gln  Gly  Glu  Glu  Ser  Asn  Asp  Lys
    1                         5

( 2 ) INFORMATION FOR SEQ ID NO:4:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Lys  Arg  Gln  His  Pro  Gly  Lys  Arg
1                    5
```

(2) INFORMATION FOR SEQ ID NO:5:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Arg  Pro  Pro  Gly  Phe  Ser  Pro  Phe  Arg
1                    5
```

(2) INFORMATION FOR SEQ ID NO:6:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Glu  His  Trp  Ser  Tyr  Gly  Leu  Arg  Pro  Gly
1                    5                         10
```

(2) INFORMATION FOR SEQ ID NO:7:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Glu  Ala  Asp  Pro  Asn  Lys  Phe  Tyr  Gly  Leu  Met
1                    5                         10
```

(2) INFORMATION FOR SEQ ID NO:8:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Asp  Arg  Val  Tyr  Ile  His  Pro  Phe  His  Leu
1                    5                         10
```

(2) INFORMATION FOR SEQ ID NO:9:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
            Pro  His  Pro  Phe  His  Phe  Phe  Val  Tyr  Lys
            1              5                        10
```

(2) INFORMATION FOR SEQ ID NO:10:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
            Asp  Val  Pro  Lys  Ser  Asp  Gln  Phe  Val  Gly  Leu  Met
            1              5                        10
```

(2) INFORMATION FOR SEQ ID NO:11:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
            Arg  Pro  Lys  Pro  Gln  Gln  Phe  Phe  Gly  Leu  Met
            1              5                        10
```

(2) INFORMATION FOR SEQ ID NO:12:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
            Cys  Gly  Tyr  Gly  Pro  Lys  Lys  Lys  Arg  Lys  Val  Gly  Gly
            1              5                        10
```

(2) INFORMATION FOR SEQ ID NO:13:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
            Gly  Ala  Pro  Val  Pro  Tyr  Pro  Asp  Pro  Leu  Glu  Pro  Arg
            1              5                        10
```

(2) INFORMATION FOR SEQ ID NO:14:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

```
Ala  Asp  Ser  Gly  Glu  Gly  Asp  Phe  Leu  Ala  Glu  Gly  Gly  Val  Arg
1                 5                      10                      15
```

( 2 ) INFORMATION FOR SEQ ID NO:15:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

```
Gly  Glu  Gln  Arg  Lys  Asp  Val  Tyr  Val  Gln  Leu  Tyr  Leu
1                 5                      10
```

( 2 ) INFORMATION FOR SEQ ID NO:16:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
Glu  Gln  Arg  Leu  Gly  Asn  Gln  Trp  Ala  Val  Gly  His  Leu  Met
1                 5                      10
```

( 2 ) INFORMATION FOR SEQ ID NO:17:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

```
Lys  Pro  Val  Gly  Lys  Lys  Arg  Arg  Pro  Val  Lys  Val  Tyr  Pro
1                 5                      10
```

( 2 ) INFORMATION FOR SEQ ID NO:18:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

```
Ser  Thr  Ser  Met  Glu  His  Phe  Arg  Trp  Gly  Lys  Pro  Val
1                 5                      10
```

( 2 ) INFORMATION FOR SEQ ID NO:19:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

```
        Asp  Arg  Val  Tyr  Ile  His  Pro  Phe  His  Leu  Leu  Val  Tyr  Ser
        1              5                        10
```

(2) INFORMATION FOR SEQ ID NO:20:

(i) SEQUENCE CHARACTERISTICS:
      (A) LENGTH: 15 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:20:

```
        Glu  Asn  Gly  Leu  Pro  Val  His  Leu  Asp  Gln  Ser  Ile  Phe  Arg  Arg
        1              5                        10                       15
```

(2) INFORMATION FOR SEQ ID NO:21:

(i) SEQUENCE CHARACTERISTICS:
      (A) LENGTH: 29 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:21:

```
        His  Ser  Gln  Gly  Thr  Phe  Thr  Ser  Asp  Tyr  Ser  Lys  Tyr  Leu  Asp  Ser
        1              5                        10                       15

Arg  Arg  Ala  Gln  Asp  Phe  Val  Gln  Trp  Leu  Met  Asn  Thr
                       20                        25
```

(2) INFORMATION FOR SEQ ID NO:22:

(i) SEQUENCE CHARACTERISTICS:
      (A) LENGTH: 32 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:22:

```
        Phe  Arg  Trp  Gly  Lys  Pro  Val  Gly  Lys  Lys  Arg  Arg  Pro  Val  Lys  Val
        1              5                        10                       15

Tyr  Pro  Asn  Gly  Ala  Glu  Asp  Glu  Ser  Ala  Glu  Ala  Phe  Pro  Leu  Glu
                       20                        25                       30
```

(2) INFORMATION FOR SEQ ID NO:23:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "NUCLEIC ACID POLYMER"

(xi) SEQUENCE DESCRIPTION: SEQ ID NO:23:

```
CGCTCTCCCT  TATGCGACTC  CTGCATTAGG  AAGCAGCCCA                                        40
```